United States Patent
Ohrui et al.

(10) Patent No.: US 7,875,368 B2
(45) Date of Patent: Jan. 25, 2011

(54) HETEROCYCLIC COMPOUND AND ORGANIC LIGHT-EMITTING DEVICE

(75) Inventors: Hiroki Ohrui, Kawasaki (JP); Akihiro Senoo, Kawasaki (JP); Tetsuya Kosuge, Kawasaki (JP); Taiki Watanabe, Akishima (JP)

(73) Assignee: Canon Kabushiki Kaisha, Tokyo (JP)

( * ) Notice: Subject to any disclaimer, the term of this patent is extended or adjusted under 35 U.S.C. 154(b) by 500 days.

(21) Appl. No.: 11/939,750

(22) Filed: Nov. 14, 2007

(65) Prior Publication Data

US 2008/0138656 A1 Jun. 12, 2008

(30) Foreign Application Priority Data

Nov. 20, 2006 (JP) .............................. 2006-312824

(51) Int. Cl.
C09K 11/00 (2006.01)
C07D 471/04 (2006.01)

(52) U.S. Cl. ........................ 428/690; 546/114; 546/115

(58) Field of Classification Search ................. 428/690; 546/115, 114
See application file for complete search history.

(56) References Cited

U.S. PATENT DOCUMENTS

| | | | |
|---|---|---|---|
| 6,171,715 B1 | 1/2001 | Sato et al. | 428/690 |
| 6,436,558 B1 | 8/2002 | Sato et al. | 428/690 |
| 6,461,747 B1 | 10/2002 | Okada et al. | 428/690 |
| 6,656,612 B2 | 12/2003 | Okada et al. | 428/690 |
| 6,830,836 B2 | 12/2004 | Okada et al. | 428/690 |
| 2002/0151720 A1* | 10/2002 | Ueno et al. | 548/152 |
| 2004/0062952 A1* | 4/2004 | Okada et al. | 428/690 |
| 2006/0115678 A1 | 6/2006 | Saitoh et al. | 428/690 |

FOREIGN PATENT DOCUMENTS

| | | |
|---|---|---|
| JP | 05-214335 | 8/1993 |
| JP | 10-340786 | 12/1998 |
| JP | 11-345686 | 12/1999 |
| JP | 2000-113985 | 4/2000 |

(Continued)

OTHER PUBLICATIONS

Mac, M.; Baran, W.; Uchacz T.; Baran, B.; Suder, M.; Lesniewski, S. Journal of Photochemistry and Photobiology A: Chemistry 192 (2007) 188-196.*

(Continued)

Primary Examiner—D. L Tarazano
Assistant Examiner—J. L. Yang
(74) Attorney, Agent, or Firm—Fitzpatrick, Cella, Harper & Scinto

(57) ABSTRACT

Provided is a novel heterocyclic compound which is useful as a material for an organic electroluminescent device. The heterocyclic compound is represented by the general formula [I]:

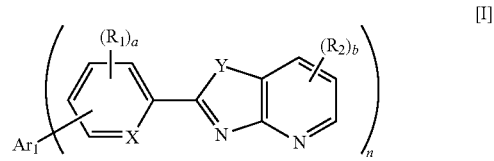

wherein X represents a nitrogen atom or a carbon atom; Y represents O or S; $R_1$ and $R_2$ each represent, independently of one another, a group selected from the group consisting of a substituted or unsubstituted alkyl group and the like; a represents 0 or more and 3 or less; b represents 0 or more and 3 or less; and $Ar_1$ represents a substituted or unsubstituted heterocyclic ring or the like; and n represents an integer of 2 to 10.

3 Claims, 3 Drawing Sheets

FOREIGN PATENT DOCUMENTS

| | | |
|---|---|---|
| JP | 2001-097961 | 4/2001 |
| JP | 2001-097962 | 4/2001 |
| JP | 2001-326079 | 11/2001 |
| JP | 2001-335776 | 12/2001 |
| JP | 2005-082703 | 3/2005 |

OTHER PUBLICATIONS

Yamamoto et al., "Composition of "Polyphosphoric Acid Trimethylsilyl Ester (PPSE)" and Its Use as a Condensation Reagent," *Chemistry Letters*, 1225-1228 (1982).

Grumel et al., "Synthesis of Substituted Oxazika[4,5-b]-Pyridine Derivatives," *Heterocycles*, vol. 55, No. 7, 1329-1345 (2001).

Couture et al., "Nouvelle Méthode de Synthèse de Thiazolopyridines," *J. Heterocyclic Chem.*, vol. 24, 1765-1769, Nov.-Dec. 1987.

Miyaura et al., "Palladium-Catalyzed Cross-Coupling Reactions of Organoboron Compounds," *Chemical Reviews*, vol. 95, No. 7, 2457-2483 (1995).

Newkome et al., "Chemistry of Heterocyclic Compound. Synthesis and Conformational Studies of Macrocycles Possessing 1,8- or 1,5-Naphthyridino Subunits Connected by Carbon-Oxygen Bridges," *J. Org. Chem.*, vol. 46, No. 5, 833-839, (1981).

* cited by examiner

HETEROCYCLIC COMPOUND AND ORGANIC LIGHT-EMITTING DEVICE

BACKGROUND OF THE INVENTION

1. Field of the Invention

The present invention relates to a novel organic compound and an organic light-emitting device using the same.

2. Description of the Related Art

The recent progress of an organic light-emitting device is significant, and the device suggests its potential to find use in a wide variety of applications because of the following reasons. The device shows high luminance at a low applied voltage. In addition, the device has a variety of emission wavelengths. Furthermore, the device can be a thin, lightweight light-emitting device with high-speed response.

However, at present, additional improvements in: initial characteristics such as emission efficiency; and duration characteristics against, for example, luminance degradation due to light emission for a long period of time have been needed. The initial characteristics and duration characteristics result from all layers constituting the device including a hole injection layer, a hole-transporting layer, a light-emitting layer, a hole-blocking layer, an electron-transporting layer, and an electron injection layer.

Examples of the hitherto known material to be used in the hole-blocking layer, the electron-transporting layer, or the electron injection layer includes, a phenanthroline compound, an aluminum quinolinol complex, an oxadiazole compound, a triazole compound, or an azole compound. There have been a relatively large number of reports each concerning the use of the azole compound out of them in a light-emitting layer, an electron-transporting layer, or an electron injection layer. Each of Japanese Patent Application Laid-Open Nos. 2005-082703, 2001-335776, 2001-326079, 2001-97961, 2001-97962, 2000-113985, H11-345686, H10-340786, and H05-214335 discloses an organic electroluminescent device using a benzoxazole compound or a heterocyclic compound having an imidazolopyridine skeleton in a light-emitting layer or an electron-transporting layer. However, the duration characteristics and initial characteristics of an EL device of each of those documents are not sufficient, and, in particular, there still remains an unsolved problem of drive at a low voltage.

SUMMARY OF THE INVENTION

An object of the present invention is to provide a novel heterocyclic compound useful as a material for an organic electroluminescent device.

Another object of the present invention is to provide an organic light-emitting device using the novel heterocyclic compound as a material for an organic electroluminescent device and having a high emission luminance and a high emission efficiency, in particular, an organic light-emitting device which is excellent in reduction of driving voltage.

Another object of the present invention is to provide an organic light-emitting device having high durability and showing less luminance degradation due to light emission for a long period of time.

Another object of the present invention is to provide an organic light-emitting device that can easily be produced at a relatively low cost.

More specifically, the present invention provides a heterocyclic compound represented by the following general formula [I]:

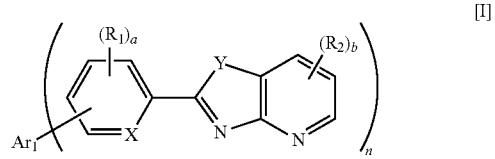

wherein X represents a nitrogen atom or a carbon atom; Y represents O or S; $R_1$ and $R_2$ each represent, independently of one another, a group selected from the group consisting of a substituted or unsubstituted alkyl group, a substituted or unsubstituted aryl group, a substituted or unsubstituted heterocyclic group, a substituted or unsubstituted fused polycyclic aromatic group, a substituted or unsubstituted fused heteropolycyclic group, a substituted or unsubstituted aryloxy group, a halogen atom, and a trifluoromethyl group; a represents 0 or more and 3 or less; and b represents 0 or more and 3 or less; $Ar_1$ represents an n-valent linking group derived from a substituted or unsubstituted aromatic ring, a substituted or unsubstituted heterocyclic ring, a substituted or unsubstituted fused polycyclic aromatic group, or a substituted or unsubstituted fused heteropolycyclic ring; and n represents an integer of 2 to 10, or by the following general formula [III]:

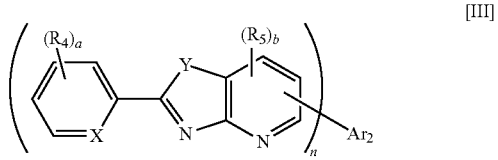

wherein X represents a nitrogen atom or a carbon atom; Y represents O or S; $R_4$ and $R_5$ each represent, independently of one another, a group selected from the group consisting of a substituted or unsubstituted alkyl group, a substituted or unsubstituted aryl group, a substituted or unsubstituted heterocyclic group, a substituted or unsubstituted fused polycyclic aromatic group, a substituted or unsubstituted fused heteropolycyclic group, a substituted or unsubstituted aryloxy group, a halogen atom, and a trifluoromethyl group; a represents 0 or more and 3 or less; b represents 0 or more and 3 or less; $Ar_2$ represents an n-valent linking group derived from a substituted or unsubstituted aromatic ring, a substituted or unsubstituted heterocyclic ring, a substituted or unsubstituted fused polycyclic aromatic group, or a substituted or unsubstituted fused heteropolycyclic ring; and n represents an integer of 2 to 10.

The heterocyclic compound of the present invention is superior to the conventional compounds in electron-transporting property, light-emitting property, durability, and, in particular, low-voltage drivability, and is useful for a layer containing an organic compound of an organic light-emitting device, in particular, an electron-transporting layer, an electron injection layer, or a hole-blocking layer. In addition, a layer formed of the compound by a vacuum vapor deposition method, a solution coating method, or the like hardly undergoes crystallization or the like, and is excellent in stability over time.

An organic light-emitting device using the heterocyclic compound of the present invention can emit light with a high luminance at a low applied voltage, and is excellent in durability. In particular, an organic layer containing the heterocyclic compound of the present invention can be excellently used as an electron-transporting layer or an electron injection layer, and can be excellently used also as a hole-blocking layer.

Further, the device can be produced by use of, for example, a vacuum vapor deposition method or a casting method, and a large-area device can easily be produced at a relatively low cost.

Further features of the present invention will become apparent from the following description of exemplary embodiments with reference to the attached drawings.

DESCRIPTION OF THE EMBODIMENTS

Figure 1:
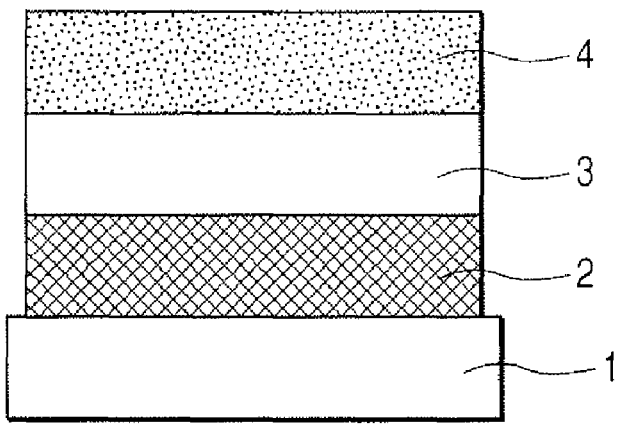
FIG. 1 is a schematic cross-sectional view illustrating an example of an organic light-emitting device according to the present invention.

Hereinafter, the present invention will be described in detail.

First, a novel heterocyclic compound of the present invention will be described.

The heterocyclic compound of the present invention is represented by the above general formula [I] or [III], and has a structure in which two or more hetero atoms are disposed on a fused heterocyclic ring so as to form a chelate structure with a metal atom.

As the heterocyclic compound of the present invention, there is included preferably a compound represented by the following general formula [II] or [IV], more preferably a compound represented by the following general formula [II].

[II]

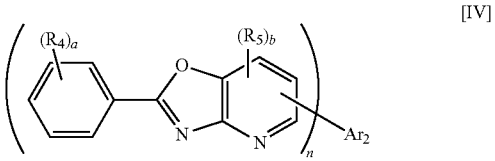

[IV]

In addition, $Ar_1$ and $Ar_2$ described above each preferably represent any one of the n-valent linking groups shown below in order that the heterocyclic compound of the present invention may have excellent electron-transporting property and excellent hole-blocking property.

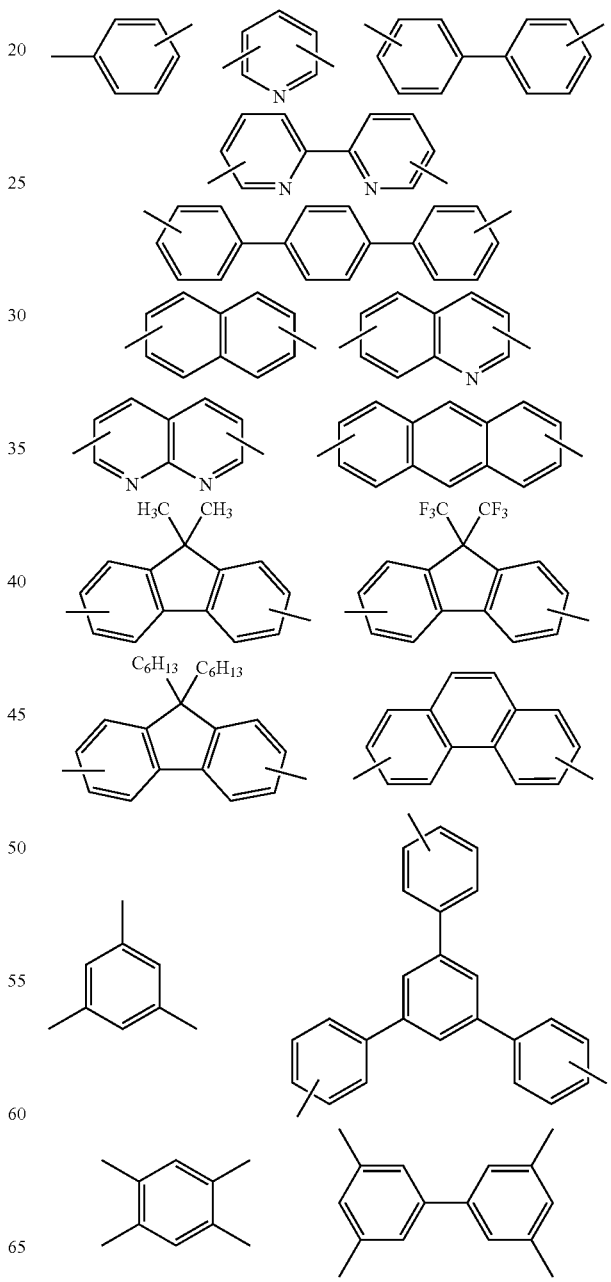

-continued

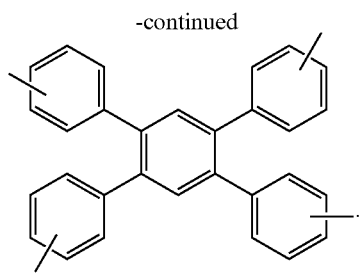

Specific examples of $R_1$ to $R_5$ in the above general formulae are shown below.

Examples of the alkyl group include, but not limited to, a methyl group, an ethyl group, an n-propyl group, an iso-propyl group, an n-butyl group, a ter-butyl group, an octyl group, and a cyclohexyl group.

Examples of the aryl group include, but not limited to, a phenyl group, a biphenyl group, and a terphenyl group.

Examples of the heterocyclic group include, but not limited to, a thienyl group, a pyrrolyl group, a pyridyl group, a bipyridyl group, and a terpyridyl group.

Examples of the fused polycyclic aromatic group include, but not limited to, a fluorenyl group, a naphthyl group, a fluoranthenyl group, an anthryl group, a phenanthryl group, a pyrenyl group, a tetracenyl group, a pentacenyl group, a perylenyl group, and a triphenylenyl group.

Examples of the fused heteropolycyclic group include, but not limited to, a quinolyl group, a carbazolyl group, an acridinyl group, a phenazyl group, a phenanthrolyl group, and a naphthyridyl group.

Examples of the aryloxy group include, but not limited to, a phenoxyl group, a fluorenoxyl group, and a naphthoxyl group.

Examples of the halogen atom include, but not limited to, fluorine, chlorine, bromine, and iodine.

Examples of the substituent each of the above substituents may have include, but not limited to, the following substituents.

Alkyl groups such as a methyl group, an ethyl group, an n-propyl group, an iso-propyl group, an n-butyl group, a ter-butyl group, and an octyl group; aryl groups such as a phenyl group, a biphenyl group, and a terphenyl group; heterocyclic groups such as a thienyl group, a pyrrolyl group, a pyridyl group, a bipyridyl group, and a terpyridyl group; fused polycyclic aromatic groups such as a fluorenyl group, a naphthyl group, a fluoranthenyl group, an anthryl group, a phenanthryl group, a pyrenyl group, a tetracenyl group, a pentacenyl group, a perylenyl group, and a triphenylenyl group; fused heteropolycyclic groups such as a quinolyl group, a carbazolyl group, an acridinyl group, a phenazyl group, a phenanthrolyl group, and a naphthyridyl group; aryloxy groups such as a phenoxyl group, a fluorenoxyl group, and a naphthoxyl group; halogen atoms such as fluorine, chlorine, bromine, and iodine; and trifluoromethyl groups and the like.

Next, representative examples of the heterocyclic compound of the present invention will be given below, but the present invention is not limited thereto.

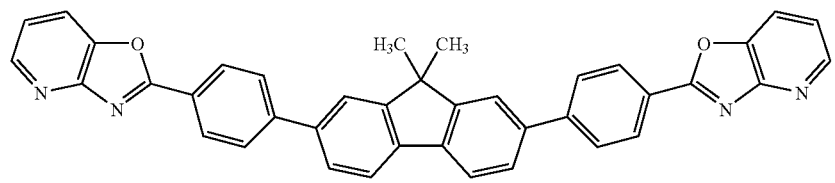

1

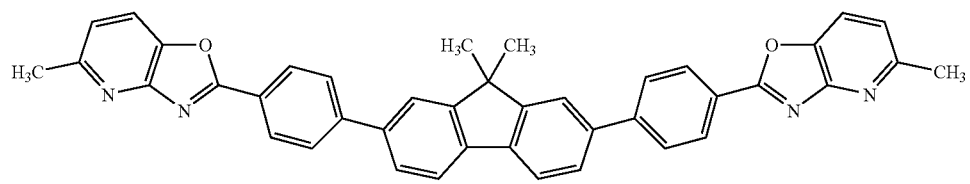

2

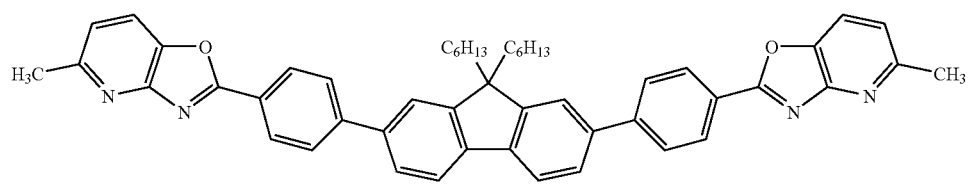

3

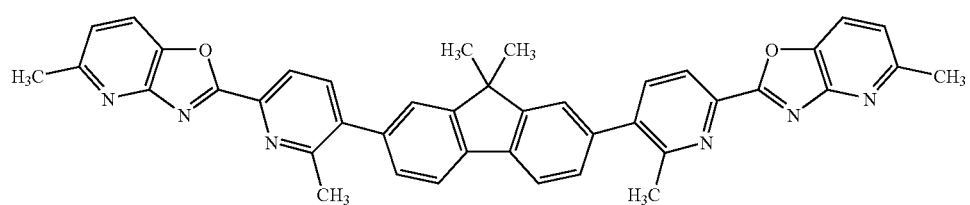

4

-continued
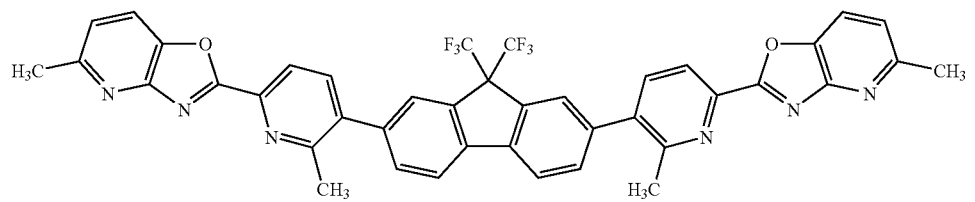
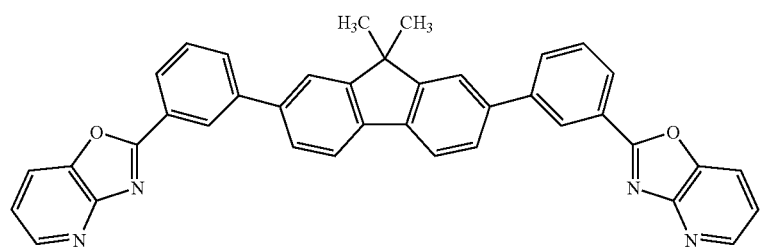
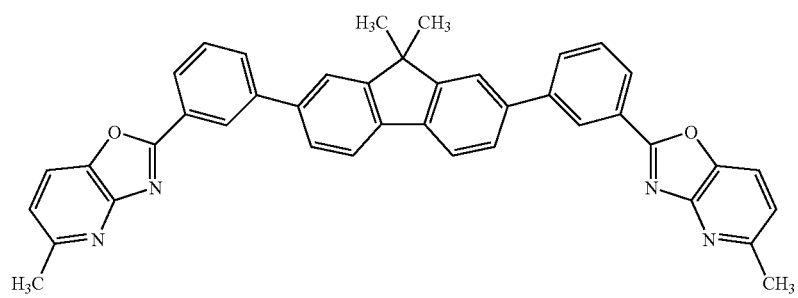
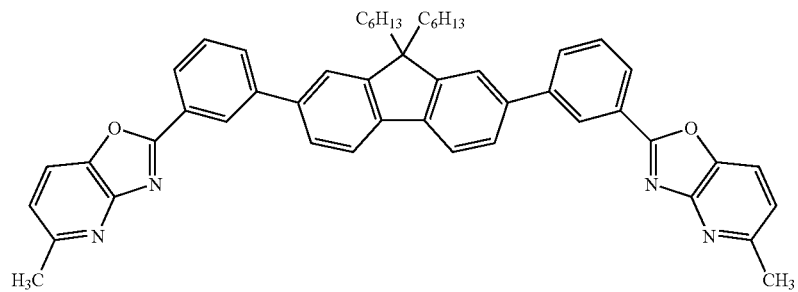
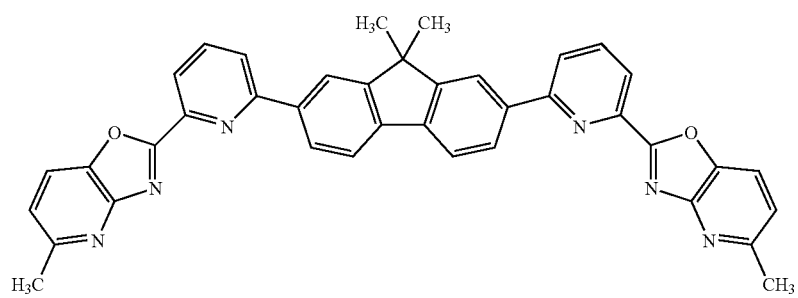
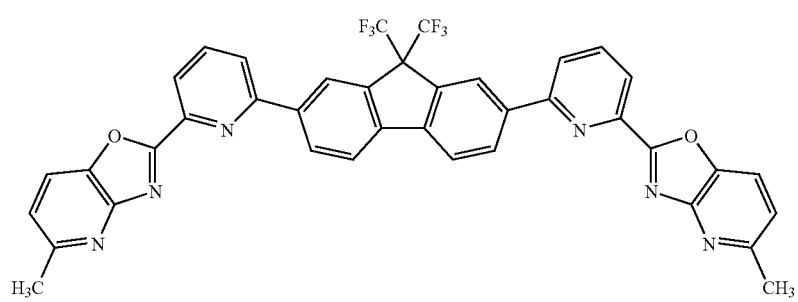

-continued
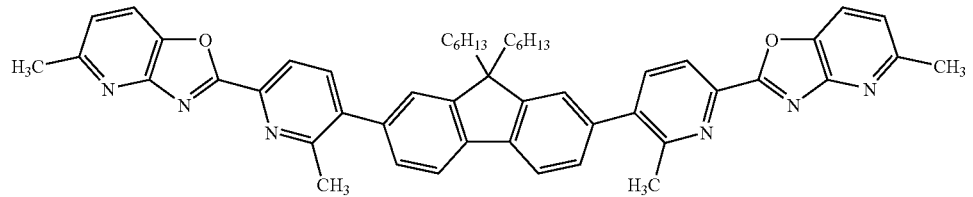
11
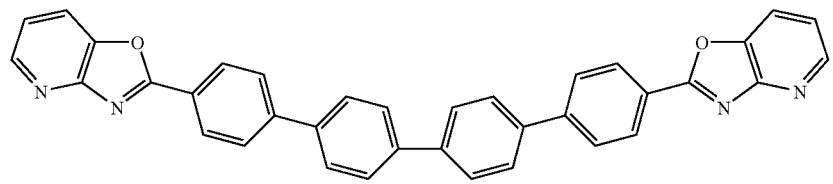
12
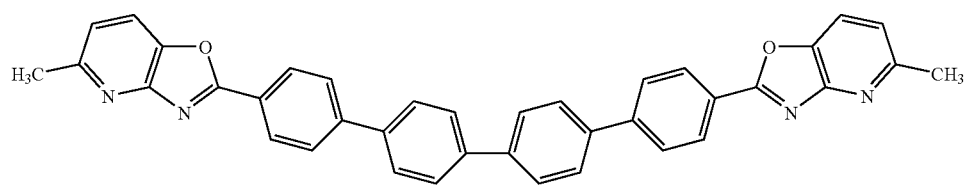
13
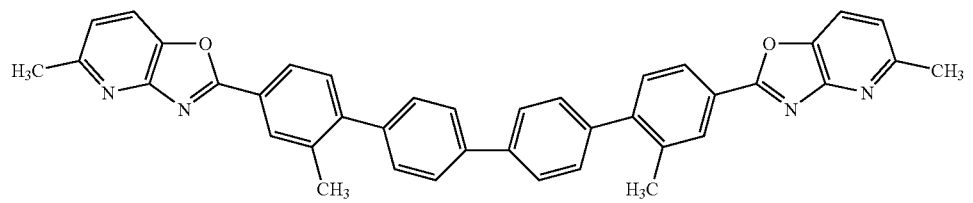
14
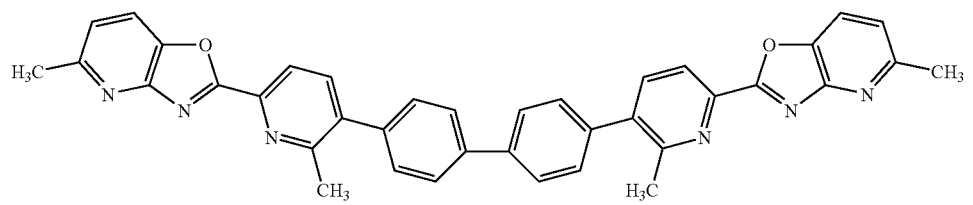
15
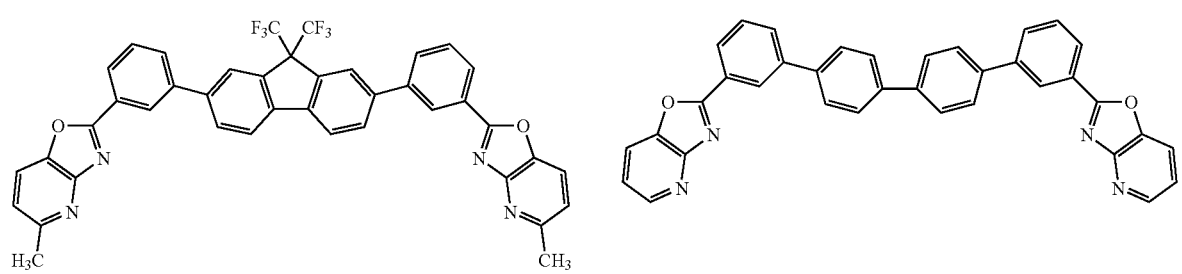
16                                              17
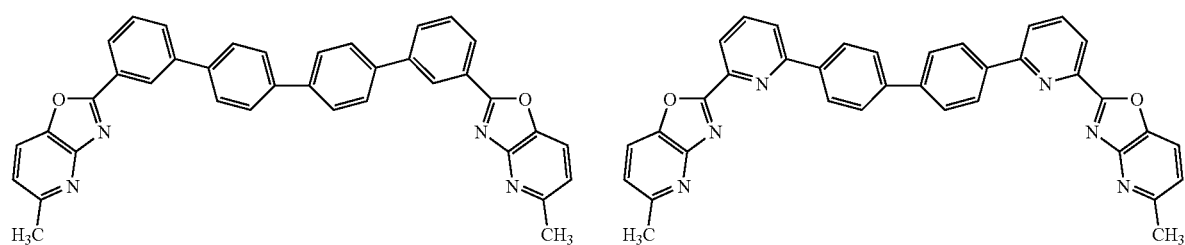
16                                              19

-continued
20
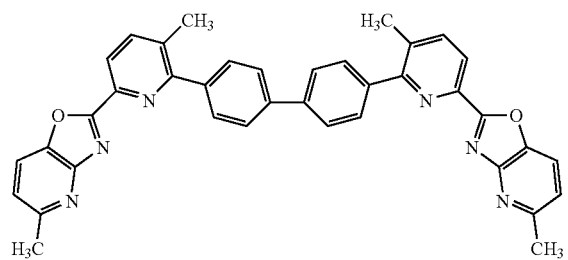
21
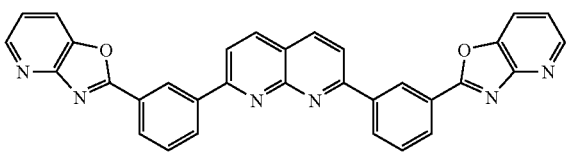
22
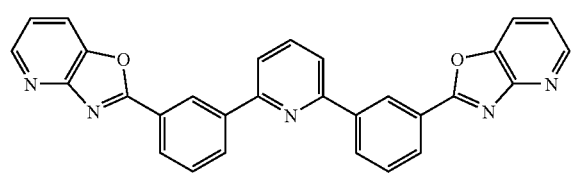
23
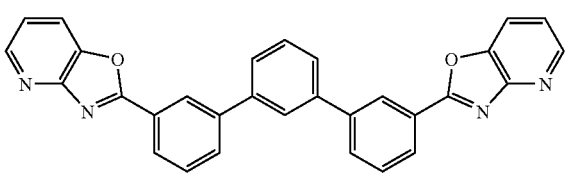
24
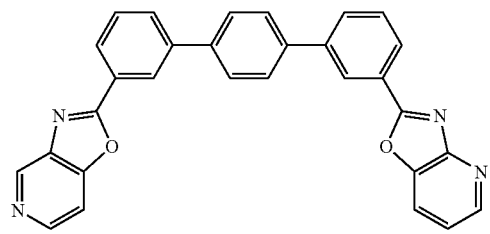
25
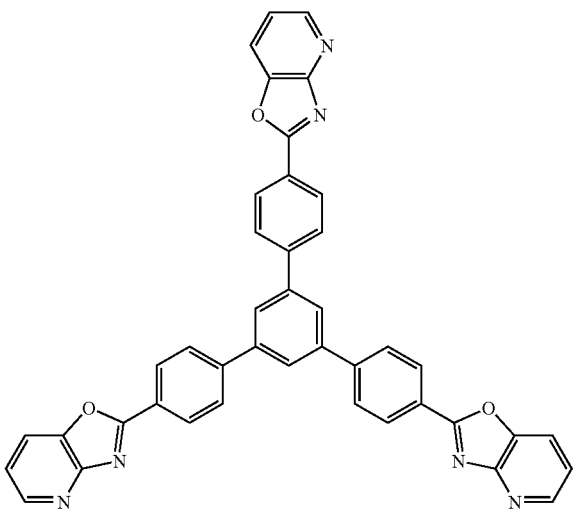
26
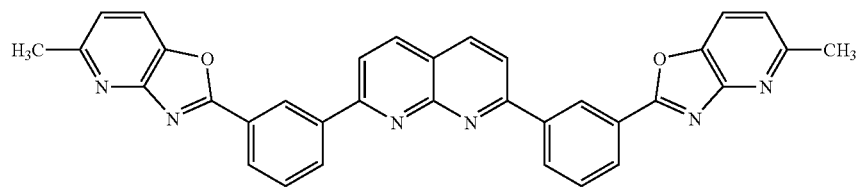
27
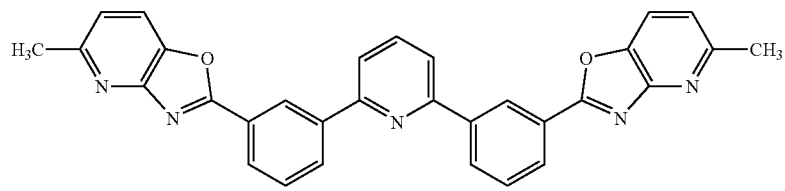
28
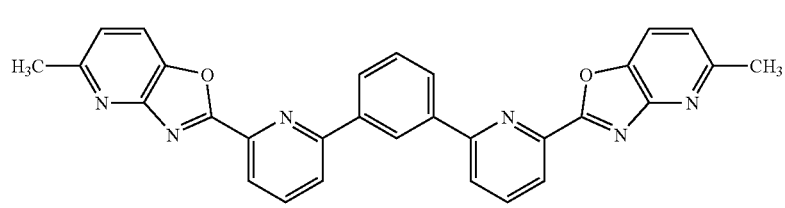

-continued
29
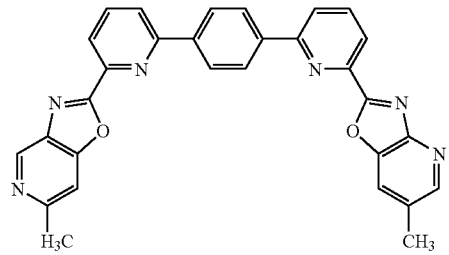
30
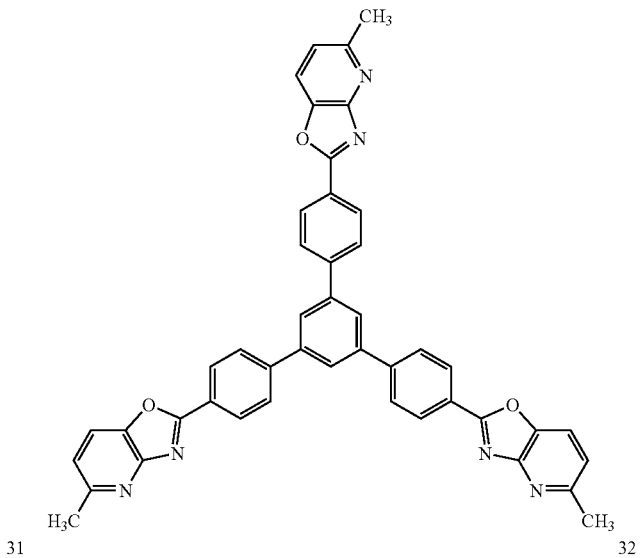
31
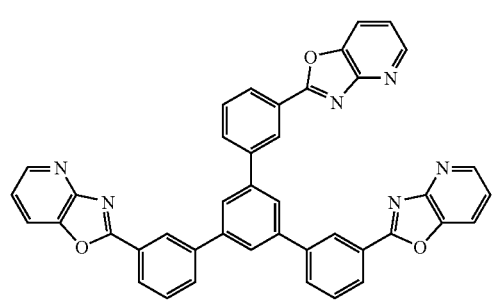
32
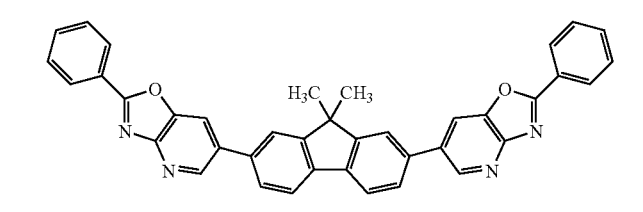
33
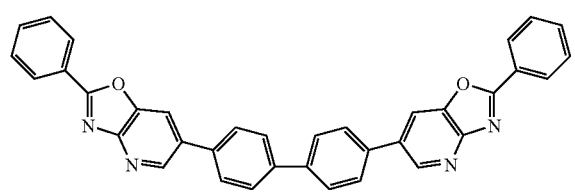
34
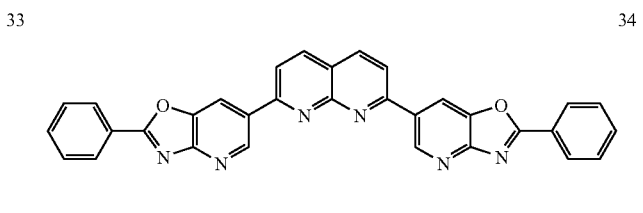
35
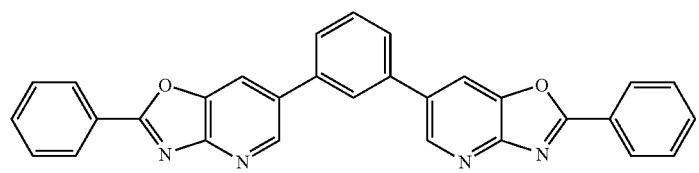
36
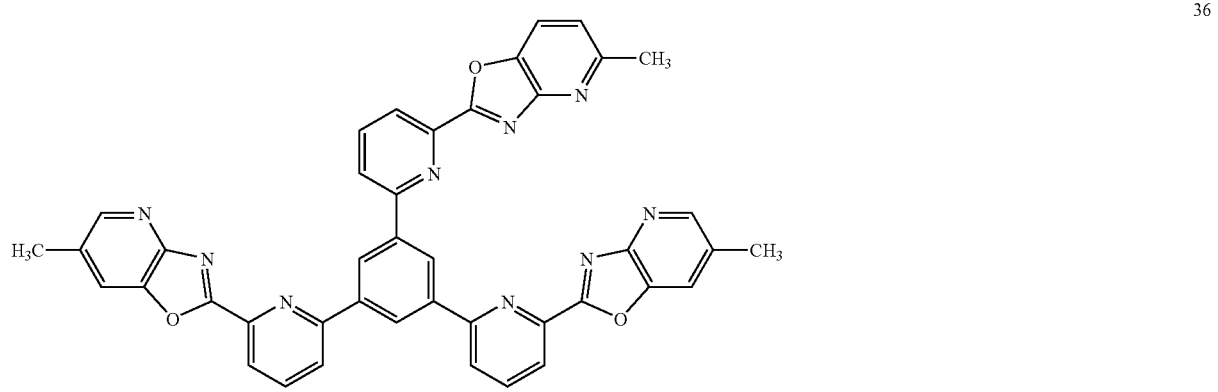

-continued
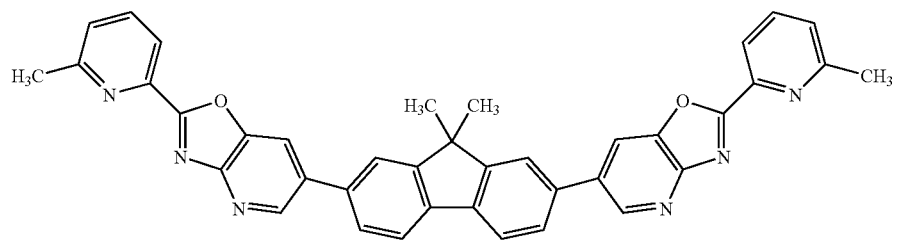
37
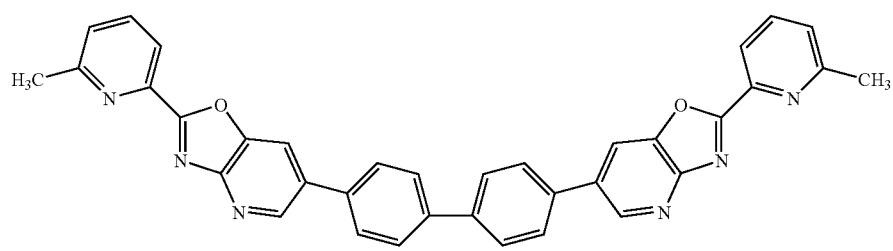
38
39
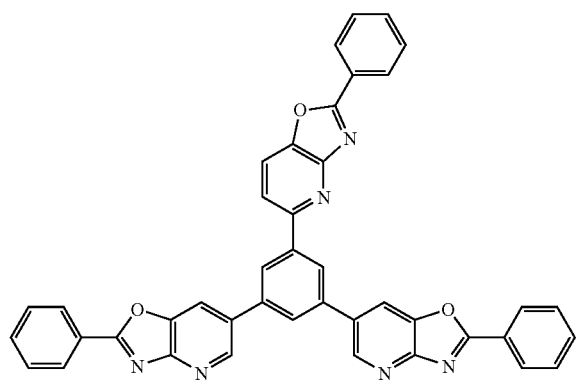
40
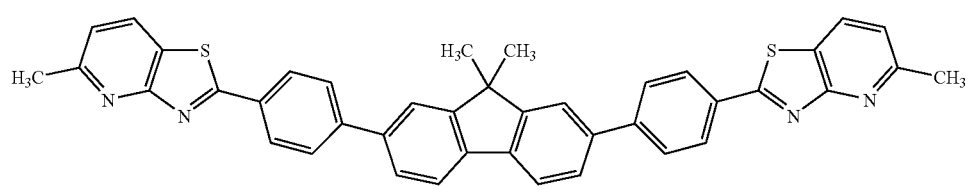
41
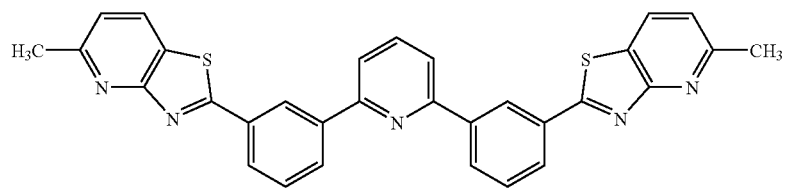
42

-continued
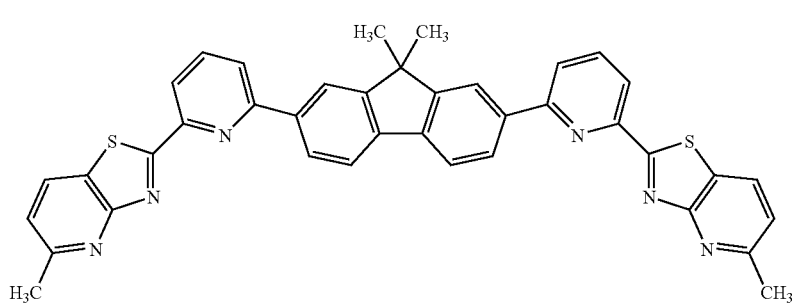
43
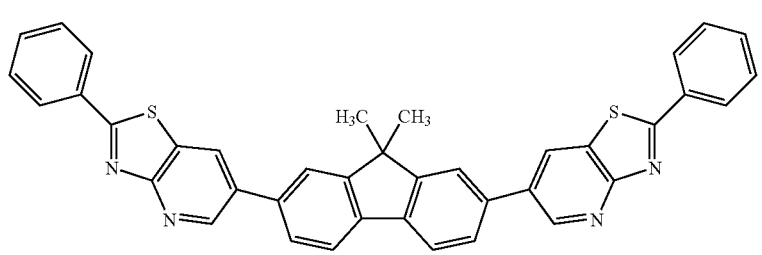
44
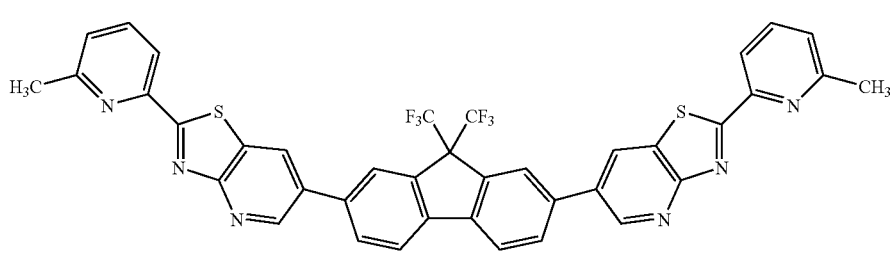
45
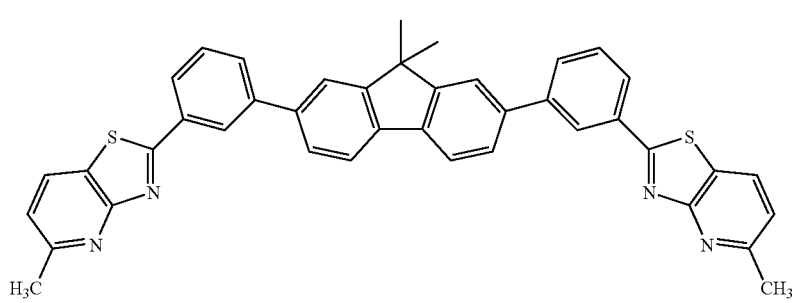
46
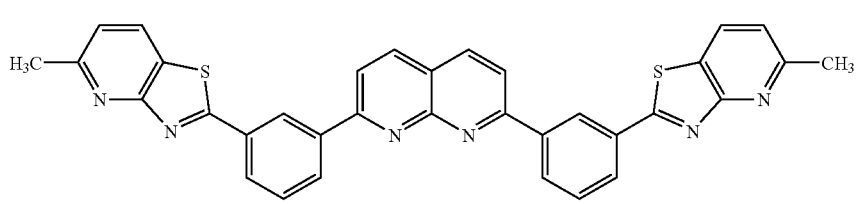
47

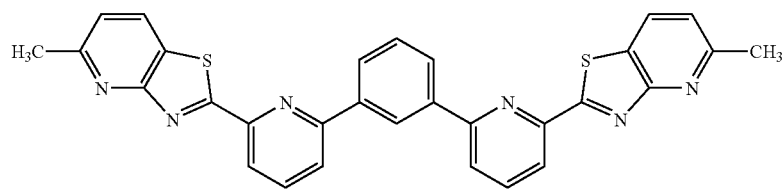

48

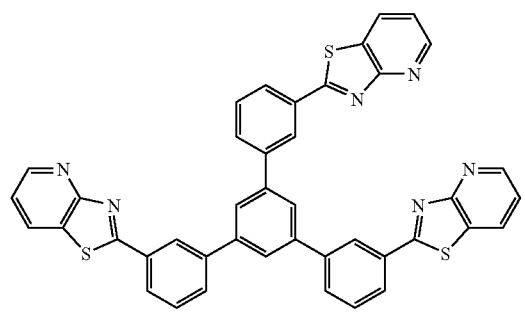

49

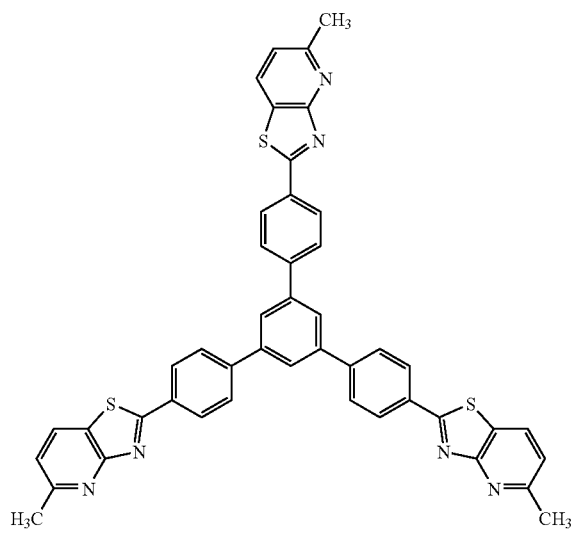

50

The heterocyclic compound of the present invention can be synthesized by a generally known method. For example, an oxazolopyridine compound intermediate or a thiazolopyridine intermediate is obtained by the methods described in the following documents: Chem. Lett, 1225 (1982), Heterocycles, 55, 1329 (2001), and Journal of Heterocyclic Chemistry, 24, 1765 (1987).

Further, the compound can be obtained by a synthesis method such as a Suzuki Coupling method (see, for example, Chem. Rev., 95, 2457, (1995)) involving the use of a palladium catalyst.

The heterocyclic compound of the present invention is superior to the conventional compounds in electron-transporting property, light-emitting property, durability, and, in particular, low-voltage drivability, and is useful for a layer containing an organic compound of an organic light-emitting device, in particular, an electron-transporting layer, an electron injection layer, or a hole-blocking layer. In addition, a layer formed of the compound by a vacuum vapor deposition method, a solution coating method, or the like hardly undergoes crystallization or the like, and is excellent in stability over time.

Next, an organic light-emitting device of the present invention will be described in detail.

An organic light-emitting device of the present invention includes at least a pair of electrodes including an anode and a cathode, and one or more layers containing an organic compound interposed between the pair of electrodes. At least one layer of the one or more layers containing an organic compound contains at least one of the heterocyclic compounds of the present invention.

In the organic light-emitting device of the present invention, it is desirable that at least one of a hole-blocking layer, an electron-transporting layer, an electron injection layer, and a light-emitting layer of the one or more layers containing an organic compound contains at least one of the heterocyclic compounds. Of the heterocyclic compounds, a compound having a relatively small HOMO has high hole-blocking property, and is particularly preferable for use in a hole-blocking layer or an electron-transporting layer.

A layer containing the heterocyclic compound of the present invention is formed between the anode and the cathode by a vacuum vapor deposition method or a solution coating method. The layer is formed in a thickness of 10 μm or less, preferably 0.5 μm or less, and more preferably 0.01 to 0.5 μm.

FIGS. 1 to 6 illustrate preferable examples of the organic light-emitting device according to the present invention.

FIG. 1 is a cross-sectional view showing an example of the organic light-emitting device according to the present invention. In FIG. 1, the device has a configuration in which an anode 2, a light-emitting layer 3, and a cathode 4 are provided sequentially on a substrate 1. A light-emitting device with this configuration is advantageous when the light-emitting material itself has all of hole transportability, electron transportability, and light-emitting property, or when compounds, respectively, having these characteristics are used in combination.

Figure 2:
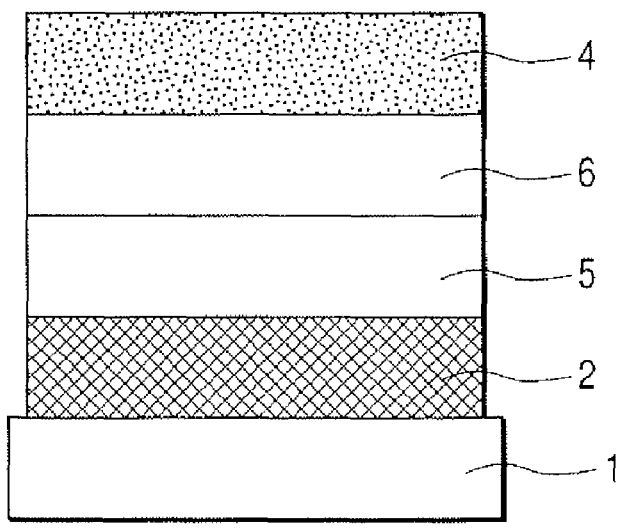
FIG. 2 is a schematic cross-sectional view illustrating another example of the organic light-emitting device according to the present invention.

FIG. 2 is a cross-sectional view showing another example of the organic light-emitting device according to the present invention. In FIG. 2, the device has a configuration such that an anode 2, a hole-transporting layer 5, an electron-transporting layer 6, and a cathode 4 are formed sequentially on a substrate 1. A light-emitting device with this configuration is advantageous when a light-emitting material having either or both of hole transportability and electron transportability is used for the respective layers, in combination with a hole-transporting material having no light-emitting property or an electron-transporting material having no light-emitting property. In addition, in this case, either one of the hole-transporting layer 5 and the electron-transporting layer 6 also serves as the light-emitting layer.

Figure 3:
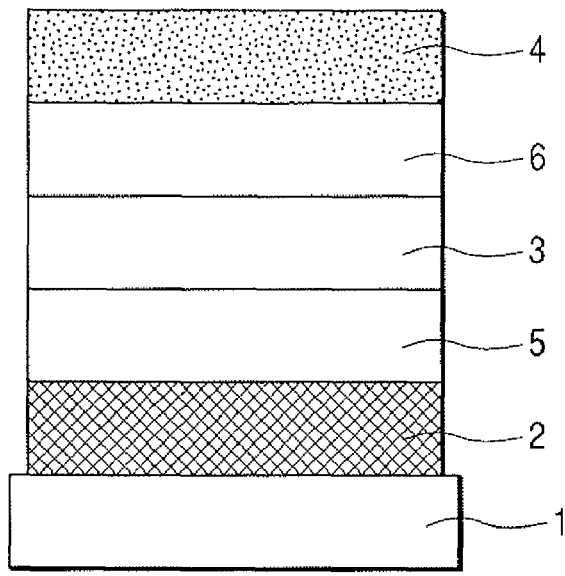
FIG. 3 is a schematic cross-sectional view illustrating still another example of the organic light-emitting device according to the present invention.

FIG. 3 is a cross-sectional view showing still another example of the organic light-emitting device according to the present invention. In FIG. 3, the device has a configuration in which an anode 2, a hole-transporting layer 5, a light-emitting layer 3, an electron-transporting layer 6, and a cathode 4 are formed sequentially on a substrate 1. With this configuration, the carrier-transporting function and the light-emitting function are separated from each other. That is, compounds, respectively, having hole-transporting property, electron-transporting property, and light-emitting property can be used appropriately in combination. As a result, the degree of freedom in selecting materials greatly increases, and various kinds of compounds having different emission wavelengths can be used, whereby a variety of emission wavelengths can be achieved. Furthermore, it also becomes possible to effectively confine carriers or excitons in the light-emitting layer at the middle portion, to thereby increase the emission efficiency.

Figure 4:
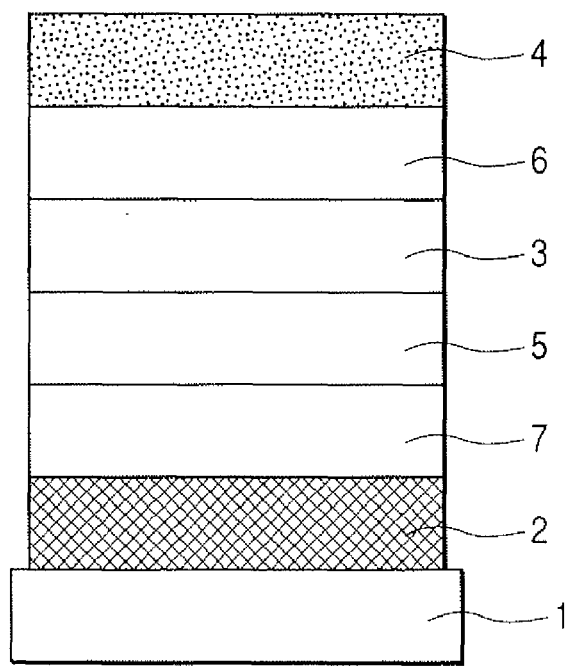
FIG. 4 is a schematic cross-sectional view illustrating yet another example of the organic light-emitting device according to the present invention.

FIG. 4 is a cross-sectional view showing still another example of the organic light-emitting device according to the present invention. In FIG. 4, as compared with FIG. 3, the device is constructed such that a hole injection layer 7 is provided on the anode side, which is effective for improving adhesion between the anode and the hole-transporting layer or improving the hole injection property, thus being effective for reducing the driving voltage.

Figure 5:
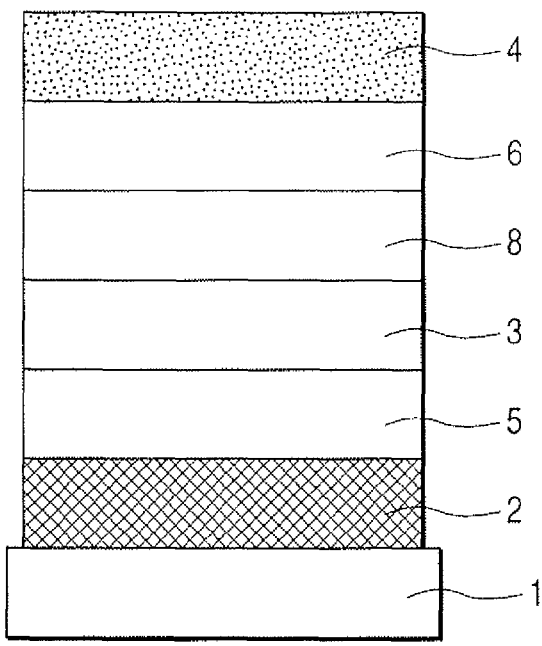
FIG. 5 is a schematic cross-sectional view illustrating yet another example of the organic light-emitting device according to the present invention.
Figure 6:
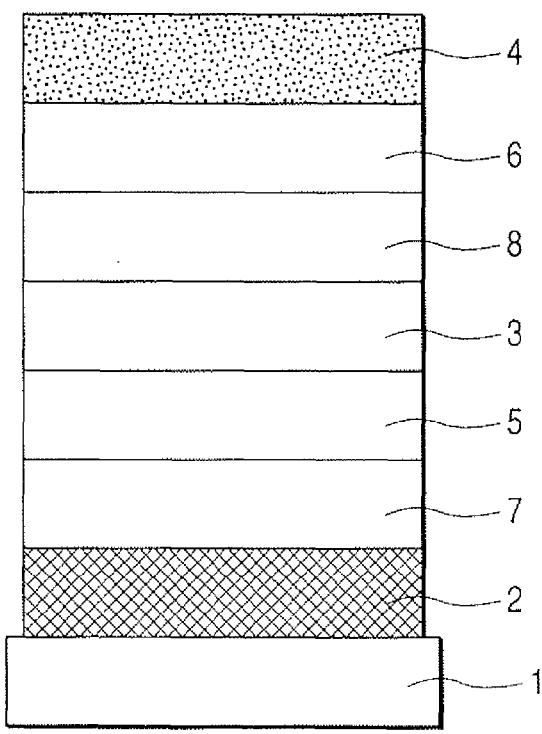
FIG. 6 is a schematic cross-sectional view illustrating yet still another example of the organic light-emitting device according to the present invention.

FIGS. 5 and 6 are cross-sectional views showing yet still other examples of the organic light-emitting device according to the present invention. In each of FIGS. 5 and 6, as compared with FIGS. 3 and 4, the device is constructed such that a layer (a hole blocking layer 8) serving to prevent holes or excitons from passing therethrough toward the cathode is provided between the light-emitting layer and the electron-transporting layer. Using a compound having an extremely high ionization potential for the hole blocking layer 8 is effective for improving the emission efficiency.

However, it is to be noted that FIGS. 1 to 6 merely show very basic device configurations, and that the structure of the organic light-emitting device using the compound according to the present invention is not limited thereto. For example, it is possible to adopt various layer configurations, such as one in which an insulating layer is provided at an interface between an electrode and an organic layer, one in which an adhesive layer or an interference layer is provided, or one in which a hole-transporting layer is composed of two layers with different ionization potentials.

The heterocyclic compound of the present invention is superior to the conventional compounds in electron-transporting property, light-emitting property, and durability, and can be used in any one of the forms shown in FIGS. 1 to 6.

In particular, an organic layer using the heterocyclic compound of the present invention is useful as a hole-blocking layer, an electron-transporting layer, or an electron injection layer. In addition, a layer formed of the compound by a vacuum vapor deposition method, a solution coating method, or the like hardly undergoes crystallization or the like, and is excellent in stability over time.

Although the organic light-emitting device of the present invention uses the heterocyclic compound of the present invention, a hitherto known hole-transporting compound, light-emitting compound, electron-transporting compound, or the like can be used together with the heterocyclic compound as needed.

Examples of those compounds will be given below.

Hole-Transporting Compound

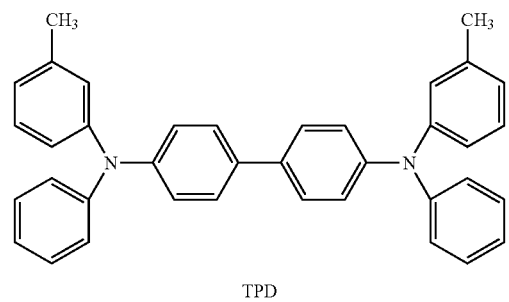

TPD

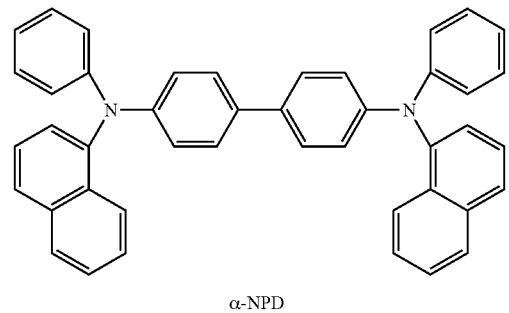

α-NPD

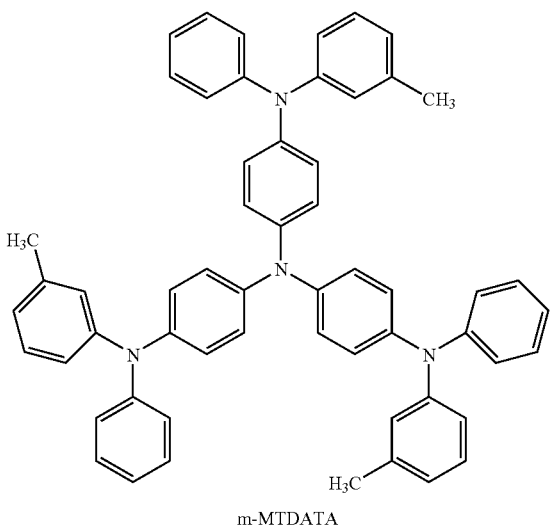

m-MTDATA

-continued
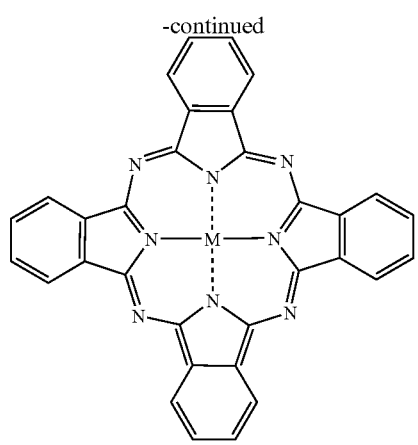
Met: Cu, Mg, AlCl, TiO, SiCl₂ etc
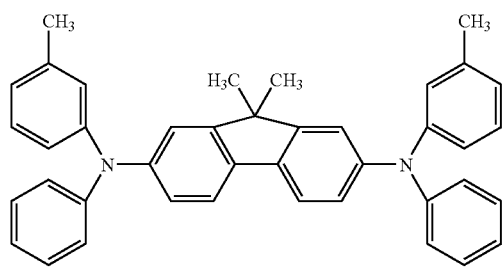
DTDPFL
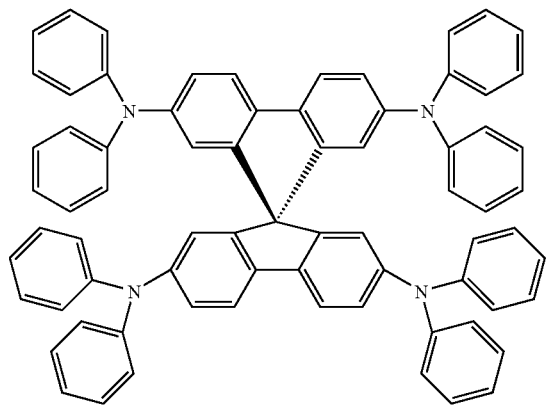
spiro-TPD
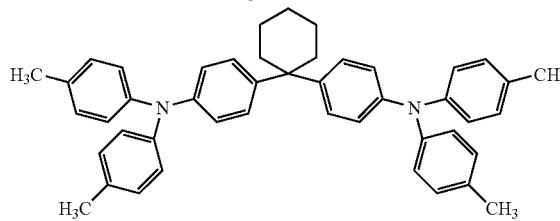
TPAC
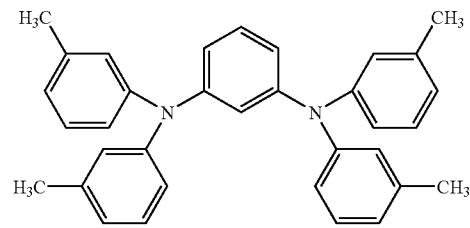
PDA
Electron-Transporting/Light-Emitting Material
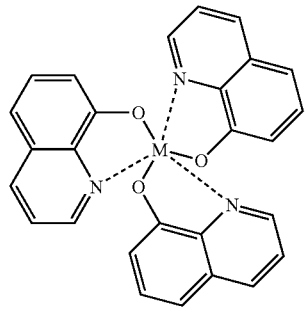
M: Al, Ga
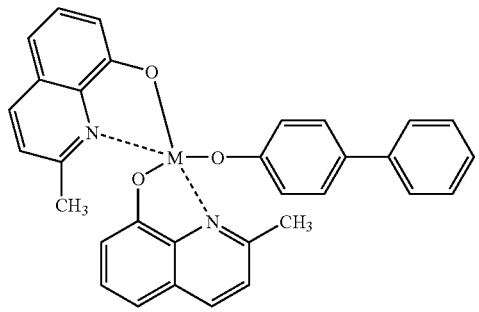
M: Al, Ga
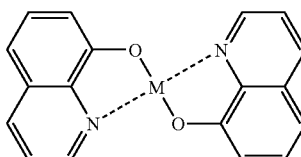
M: Zn, Mg, Be
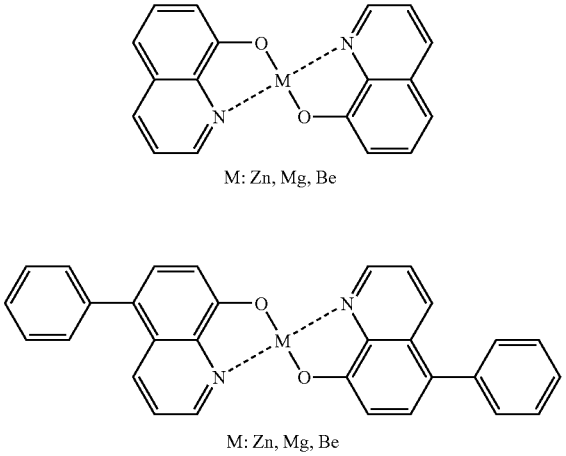
M: Zn, Mg, Be
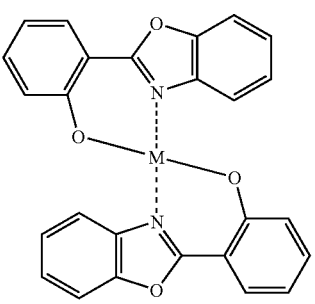
M: Zn, Mg, Be -continued
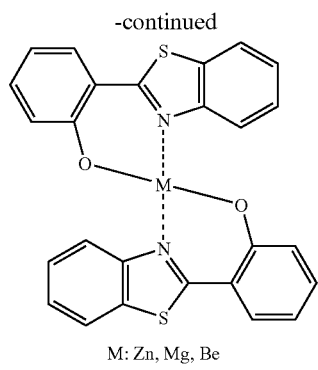
M: Zn, Mg, Be
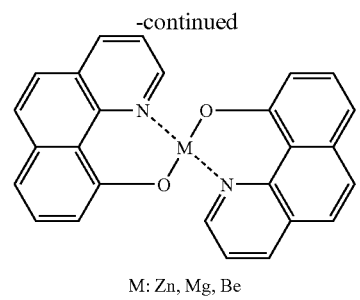
M: Zn, Mg, Be
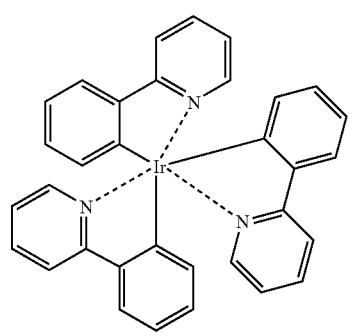
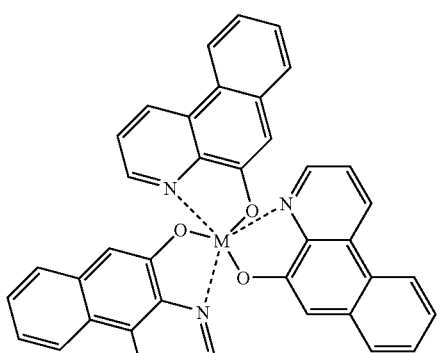
M: Al, Ga
Light-Emitting Material
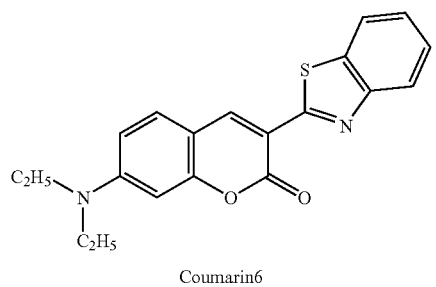
Coumarin6
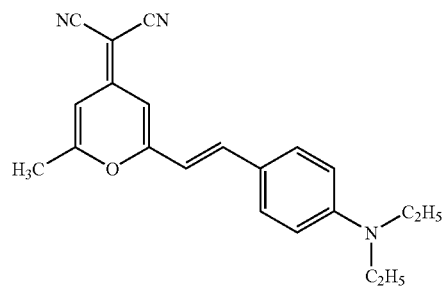
DCM-1
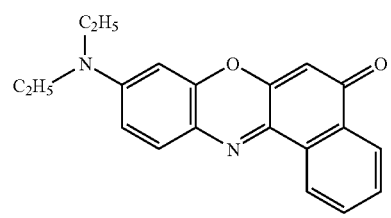
Nile red
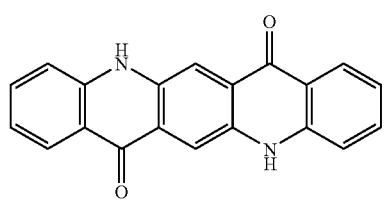
Quinacridone -continued
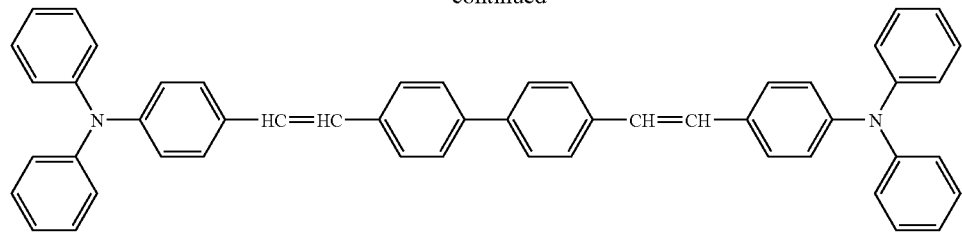
DTPABVi
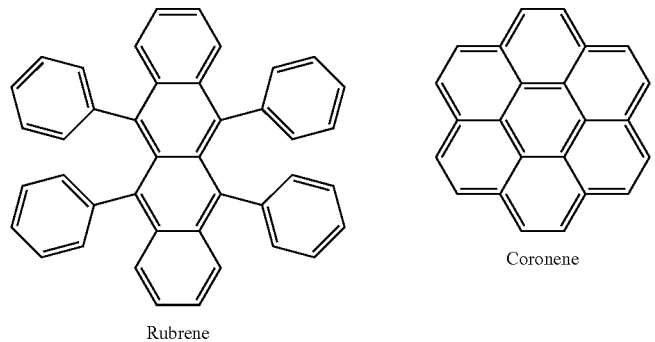
Rubrene
Coronene
Light-Emitting Layer Matrix Material and Electron-Transporting Material
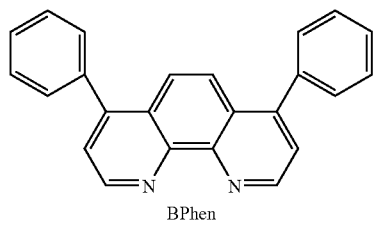
BPhen
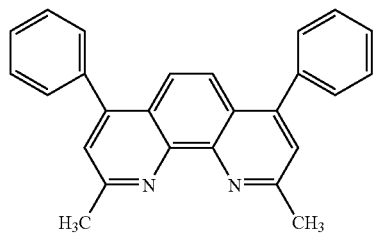
BCP
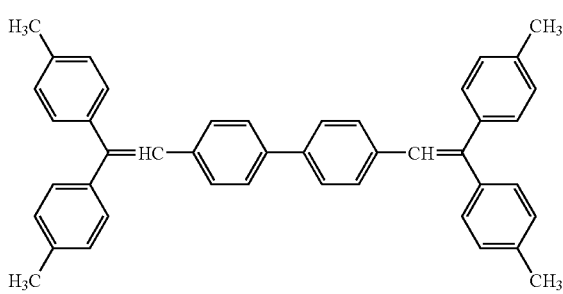
-continued
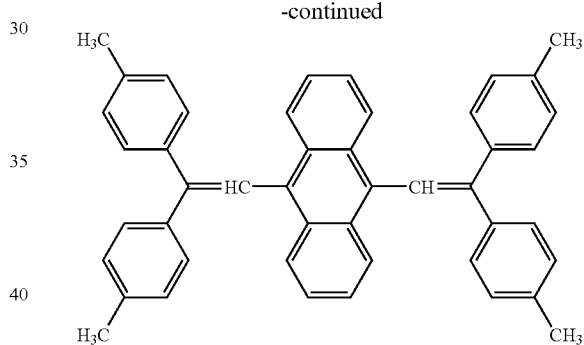
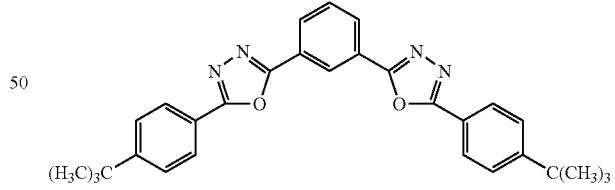
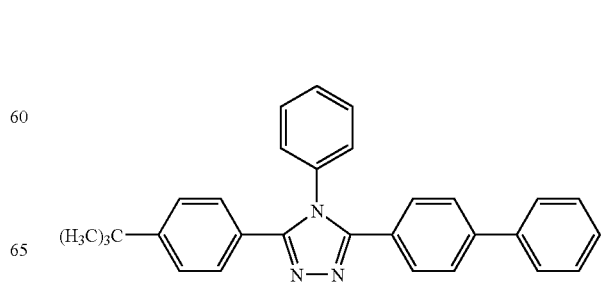

-continued
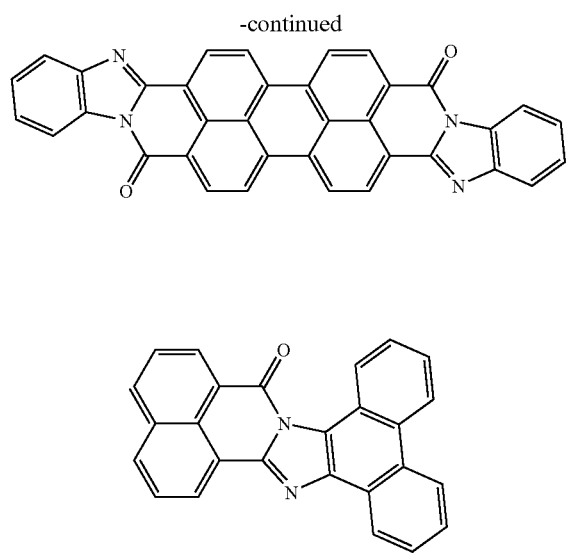
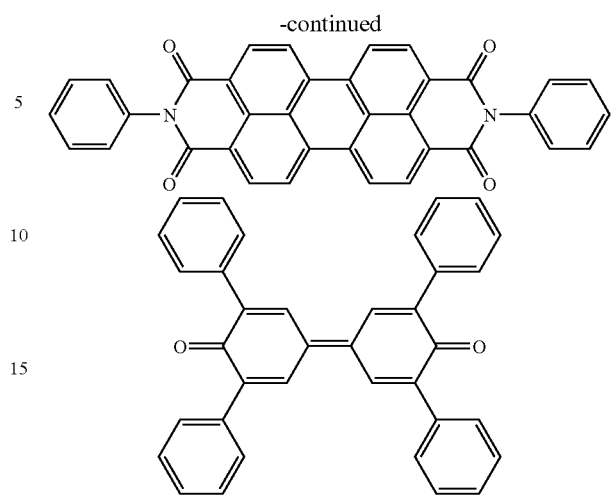
Polymeric Hole-Transporting Material
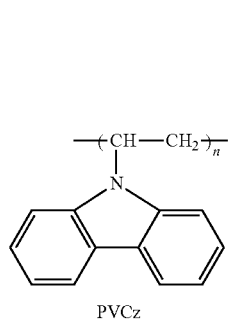
PVCz
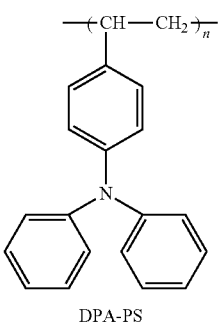
DPA-PS
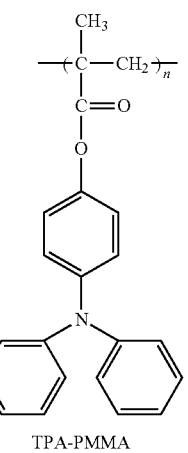
TPA-PMMA
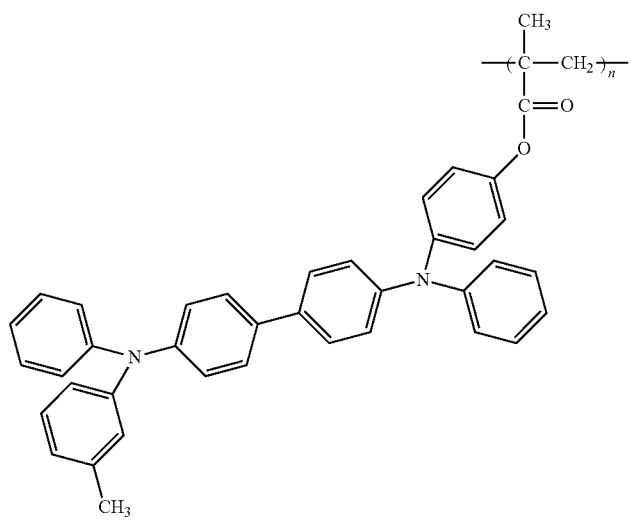
TPD-PMMA

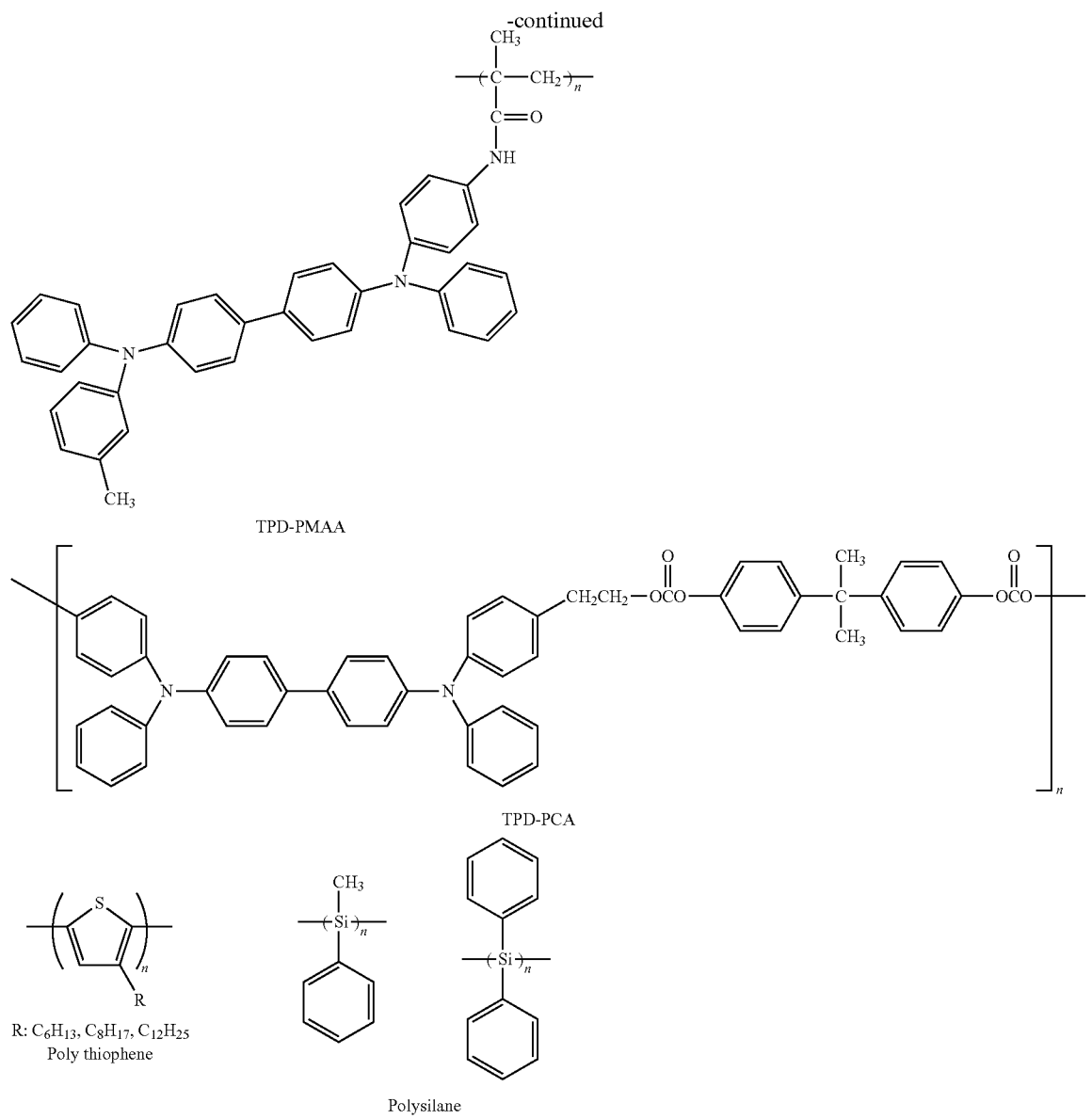
Polymeric Light-Emitting Material and Charge-Transporting Material
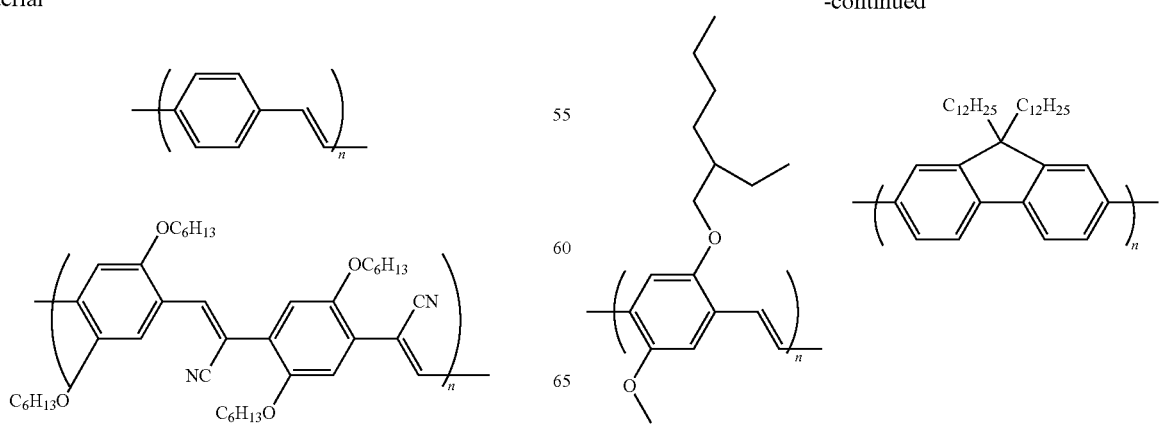

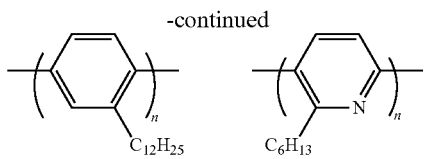

In the organic light-emitting device of the present invention, the layer containing the heterocyclic compound of the present invention and the other layers comprising an organic compound are formed as a thin film generally by using a vacuum deposition method or a coating method of applying such organic compound dissolved in a suitable solvent. Particularly, when the film is formed by the coating method, the film can be formed by additionally using a suitable binder resin.

The above-mentioned binder resin can be selected from a wide range of binding resins, and includes, for instance, polyvinylcarbazole resin, polycarbonate resin, polyester resin, polyarylate resin, polystyrene resin, acrylic resin, methacrylic resin, butyral resin, polyvinylacetal resin, diallylphthalate resin, phenolic resin, epoxy resin, silicone resin, polysulfonic resin and urea resin, but is not limited thereto. In addition, the binder resin may be singly used, or be used in combination as a copolymer.

An anode material used preferably has as large a work function as possible, and includes, for instance, an elemental metal such as gold, platinum, nickel, palladium, cobalt, selenium, and vanadium, an alloy thereof, and a metal oxide such as stannic oxide, zinc oxide, indium tin oxide (ITO) and indium zinc oxide. Further, a conductive polymer such as polyaniline, polypyrrole, polythiophene, and polyphenylene sulfide can be employed. These electrode materials can be used singly or in combination.

On the other hand, a cathode material used preferably has a low work function, and includes, for instance an elemental metal such as lithium, sodium, potassium, cesium, calcium, magnesium, aluminum, indium, silver, lead, tin, and chromium; or an alloy made of a plurality of the above metals. A metal oxide such as indium tin oxide (ITO) can be also used. In addition, the cathode may be either of a single layer configuration or of a multilayer configuration.

A substrate used in the present invention is not particularly limited, but an opaque substrate such as a metal substrate and a ceramic substrate or a transparent substrate such as glass, quartz, and a plastic sheet is used. Further, it is also possible to employ, for a substrate, a color filter film, a fluorescent color conversion filter film and a dielectric reflective film to thereby control the emission color.

Incidentally, after a device has been produced, a protective layer or an encapsulation layer may further be provided, for the purpose of preventing contact with oxygen or moisture. Examples of such a protective layer include a diamond thin film; a film of an inorganic material such as a metal oxide and a metal nitride; a film of a polymer such as a fluororesin, poly-p-xylene, polyethylene, silicone resin, and polystyrene resin; and further a film of a photocurable resin. Further, the produced device may also be covered with glass, a gas-impermeable film and a metal, or be packaged with a suitable encapsulation resin.

EXAMPLE

Hereinafter, the present invention will be described more specifically by way of examples. However, the present invention is not limited to these examples.

Synthesis Example 1

Synthesis of Exemplified Compound No. 1

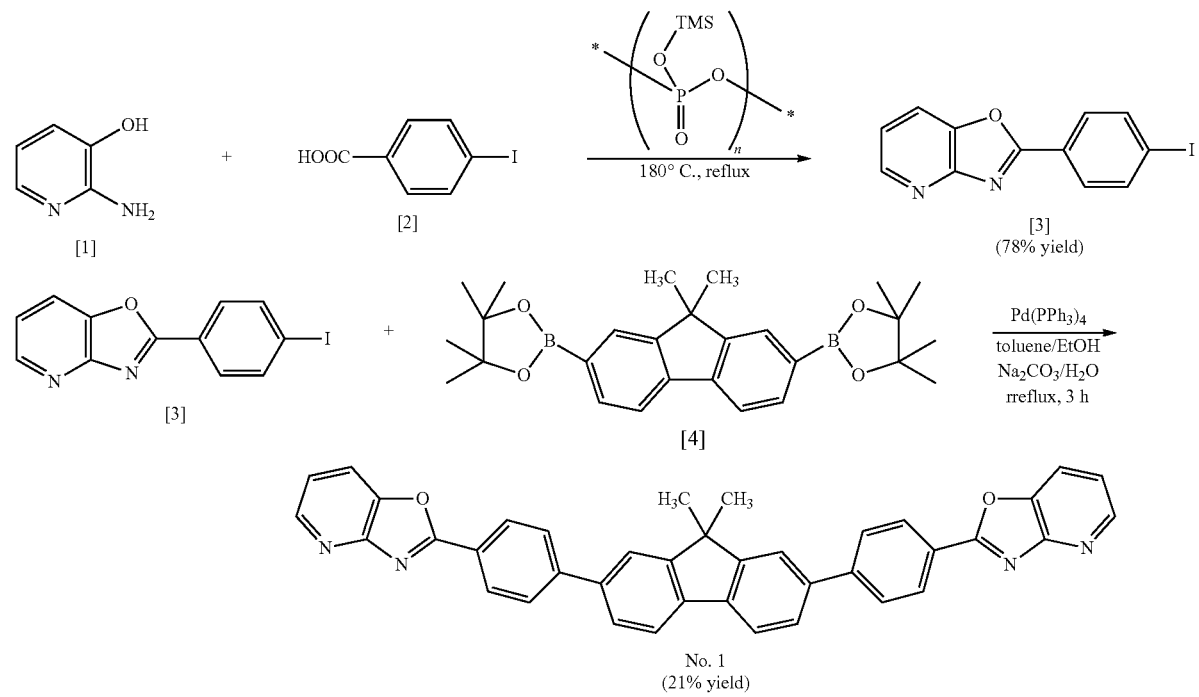

2-(4-iodophenyl)-oxazolo-[4,5-b]pyridine [3] (pale yellow crystal) was obtained from 3-hydroxy-2-aminopyridine [1] and 4-iodobenzoic acid [2] in 78% yield by the synthesis method described in the following document: Heterocycles, 55, 1329 (2001).

The following compounds were placed in a 200-ml three-necked flask, and the mixture was stirred under nitrogen atmosphere at room temperature. During the stirring, an aqueous solution of 2 g of sodium carbonate in 20 ml of water was added dropwise to the mixture.

1.59 g (4.94 mmol) of 2-(4-iodophenyl)-oxazolo-[4,5-b]pyridine [3]
1.00 g (2.24 mmol) of a 9,9-dimethylfluorene-2,7-diboronic acid pinacol ester [4]
50 ml of toluene and 25 ml of ethanol Next, 0.25 g (0.22 mmol) of tetrakis(triphenylphosphine) palladium(0) was added to the mixture. After the mixture was stirred at room temperature for 10 minutes, the temperature of the mixture was increased to 78° C., and the mixture was stirred under heating and reflux for 3 hours. The reaction liquid was filtrated, and the resultant crude product was dissolved in 450 ml of chloroform at 70° C. The solution was purified with a silica gel column (chloroform/methanol=40/1), whereby 0.27 g of Exemplified Compound No. 1 (white crystal) was obtained (21% yield).

Synthesis Example 2

Synthesis of Exemplified Compound No. 25

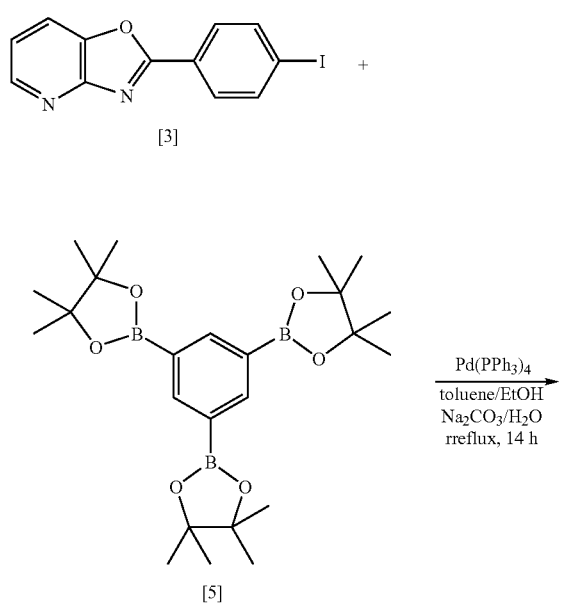

[3]

[5]

Pd(PPh3)4
toluene/EtOH
Na2CO3/H2O
rreflux, 14 h

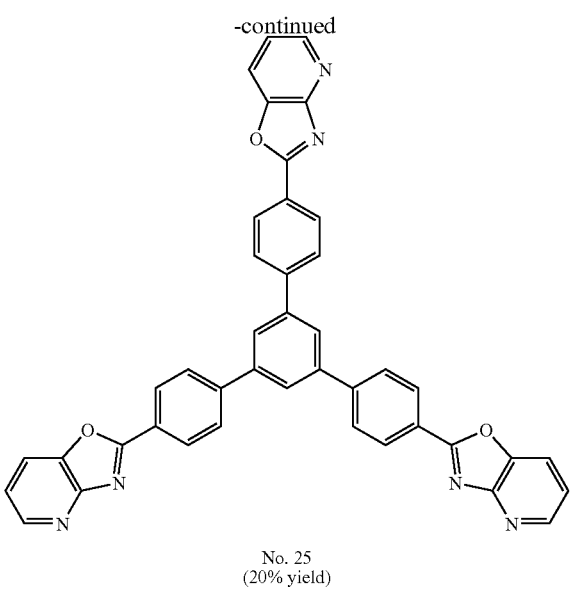

No. 25
(20% yield)

The following compounds were placed in a 50-ml three-necked flask, and the mixture was stirred under nitrogen atmosphere at room temperature. During the stirring, an aqueous solution of 0.8 g of sodium carbonate in 8 ml of water was added dropwise to the mixture.

1.62 g (5.03 mmol) of 2-(4-iodophenyl)-oxazolo-[4,5-b]pyridine [3]
0.41 g (0.90 mmol) of a tripinacol [5]
20 ml of toluene and 10 ml of ethanol Next, 0.40 g (0.34 mmol) of tetrakis(triphenylphosphine) palladium(0) was added to the mixture. After the mixture was stirred at room temperature for 10 minutes, the temperature of the mixture was increased to 78° C., and the mixture was stirred under heating and reflux for 14 hours. The reaction liquid was filtrated, and the resultant crude product was dissolved in 450 ml of chloroform at 70° C. The solution was purified with a silica gel column (chloroform/methanol 30/1), whereby 0.12 g of Exemplified Compound No. 25 (white crystal) was obtained (20% yield).

Synthesis Example 3

Synthesis of Exemplified Compound No. 2

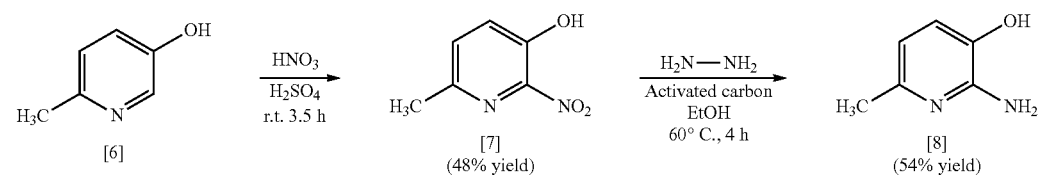

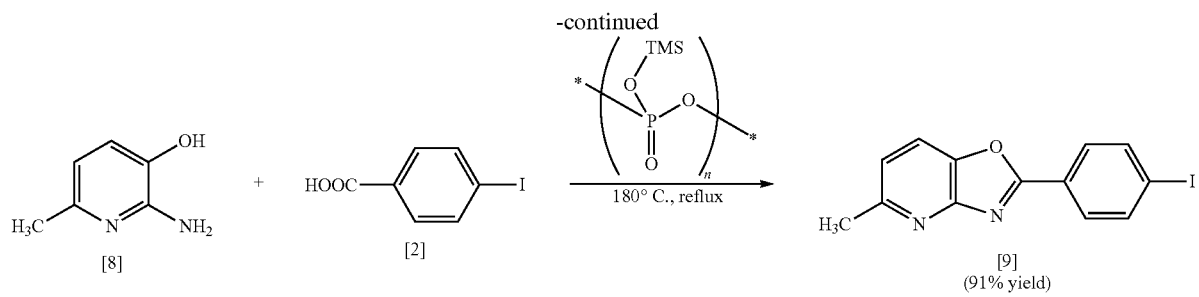

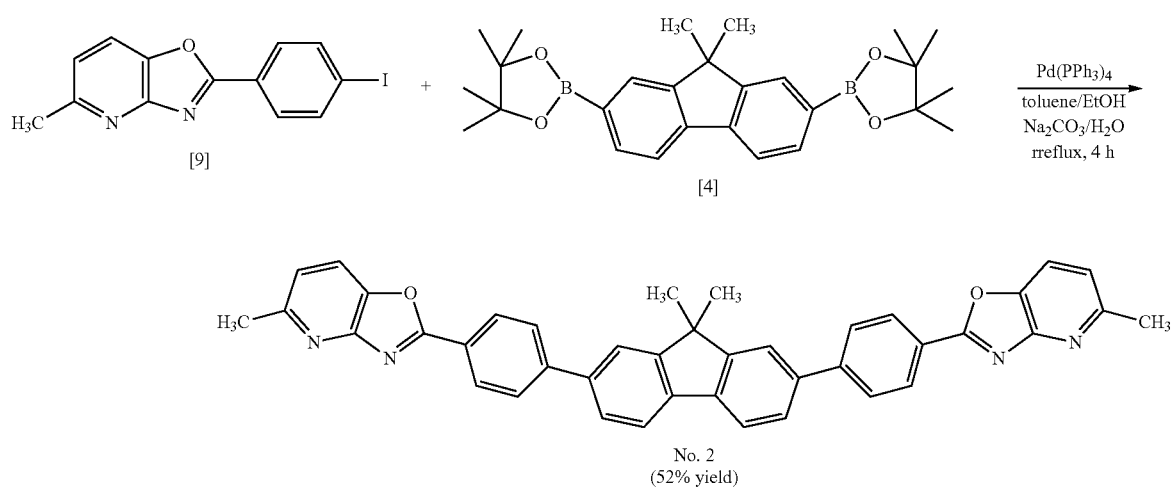

No. 2
(52% yield)

6-methyl-2-amino-pyridin-3-ol [8] was obtained from 6-methyl-pyridin-3-ol [6] in a total yield of 26% by a known method described in a document.

2-(4-iodophenyl)-5-methyl-oxazolo-[4,5-b]pyridine [9] (pale yellow crystal) was obtained from 6-methyl-2-amino-pyridine [8] and 4-iodobenzoic acid [2] in 91% yield by following the same procedure as in Synthesis Example 1.

The following compounds were placed in a 200-ml three-necked flask, and the mixture was stirred under nitrogen atmosphere at room temperature. During the stirring, an aqueous solution of 2 g of sodium carbonate in 20 ml of water was added dropwise to the mixture.

1.66 g (4.94 mmol) of 2-(4-iodophenyl)-5-oxazolo-[4,5-b] pyridine [9]

1.00 g (2.24 mmol) of a 9,9-dimethylfluorene-2,7-diboronic acid pinacol ester [4]

50 ml of toluene and 25 ml of ethanol

Next, 0.25 g (0.22 mmol) of tetrakis(triphenylphosphine) palladium(0) was added to the mixture. After the mixture had was stirred at room temperature for 10 minutes, the temperature of the mixture was increased to 78° C., and the mixture was stirred under heating and reflux for 4 hours. The reaction liquid was filtrated, and the resultant crude product was dissolved in 450 ml of chloroform at 70° C. The solution was purified with a silica gel column (chloroform/methanol=40/1), whereby 0.71 g of Exemplified Compound No. 2 (white crystal) was obtained (52% yield).

Synthesis Example 4

Synthesis of Exemplified Compound No. 6

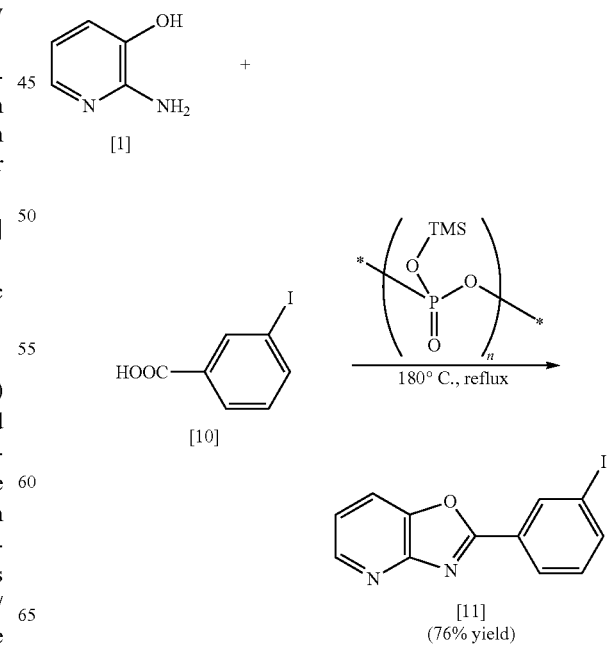

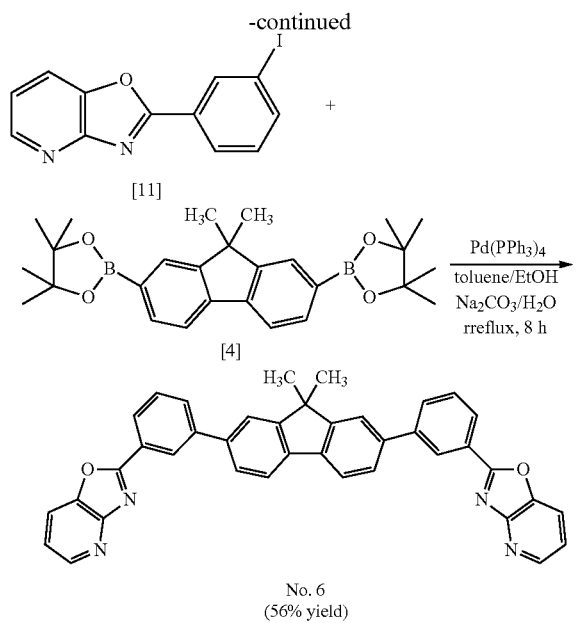

2-(3-iodophenyl)-oxazolo-[4,5-b]pyridine [11] (pale yellow crystal) was obtained from 2-amino-pyridine-3-ol [1] and 3-iodobenzoic acid [10] in 76% yield in the same manner as in Synthesis Example 1.

The following compounds were placed in a 200-ml three-necked flask, and the mixture was stirred under nitrogen atmosphere at room temperature. During the stirring, an aqueous solution of 2 g of sodium carbonate in 20 ml of water was added dropwise to the mixture.

1.59 g (4.79 mmol) of 2-(3-iodophenyl)-oxazolo-[4,5-b]pyridine [11]

1.00 g (2.24 mmol) of a 9,9-dimethylfluorene-2,7-diboronic acid pinacol ester [4]

50 ml of toluene and 25 ml of ethanol

Next, 0.50 g (0.44 mmol) of tetrakis(triphenylphosphine) palladium(0) was added to the mixture. After the mixture was stirred at room temperature for 10 minutes, the temperature of the mixture was increased to 78° C., and the mixture was stirred under heating and reflux for 8 hours. The reaction liquid was filtrated, and the resultant crude product was dissolved in 150 ml of chloroform at 70° C. The solution was purified with a silica gel column (chloroform/methanol=50/1), whereby 0.73 g of Exemplified Compound No. 6 (white crystal) was obtained (56% yield).

Synthesis Example 5

Synthesis of Exemplified Compound No. 22

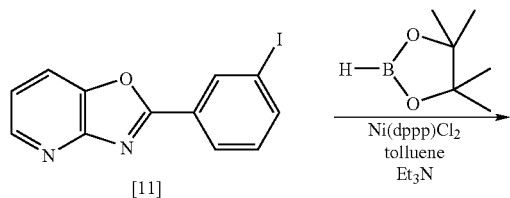

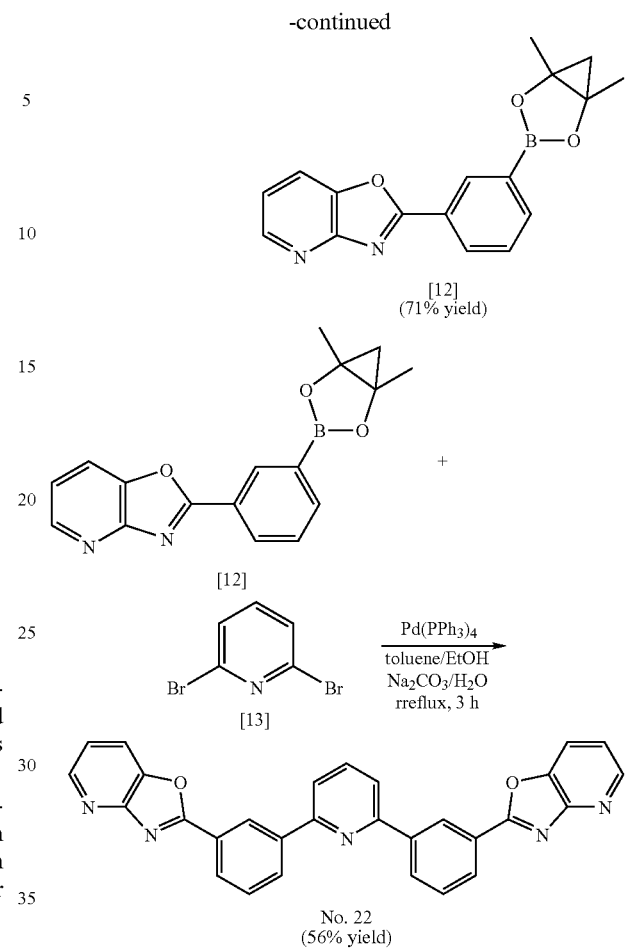

2-(3-iodophenyl)-oxazolo-[4,5-b]pyridine [11] obtained in Synthesis Example 4 was transformed into the corresponding boronic acid pinacol ester [12] according to a known method described in a document, whereby a white crystal was obtained in 71% yield.

The following compounds were placed in a 100-ml three-necked flask, and the mixture was stirred under nitrogen atmosphere at room temperature. During the stirring, an aqueous solution of 1 g of sodium carbonate in 10 ml of water was added dropwise to the mixture.

1.50 g (4.66 mmol) of boronic acid pinacol ester [12]

0.50 g (2.11 mmol) of a 2,6-dibromopyridine [13]

25 ml of toluene and 13 ml of ethanol

Next, 0.24 g (0.21 mmol) of tetrakis(triphenylphosphine) palladium(0) was added to the mixture. After the mixture was stirred at room temperature for 10 minutes, the temperature of the mixture was increased to 78° C., and the mixture was stirred under heating and reflux for 2 hours. The reaction liquid was filtrated, and the resultant crude product was dissolved in 200 ml of chloroform at 70° C. The solution was purified with a silica gel column (chloroform/methanol=30/1), whereby 0.55 g of Exemplified Compound No. 22 (white crystal) was obtained (56% yield).

Synthesis Example 6

Synthesis of Exemplified Compound No. 21

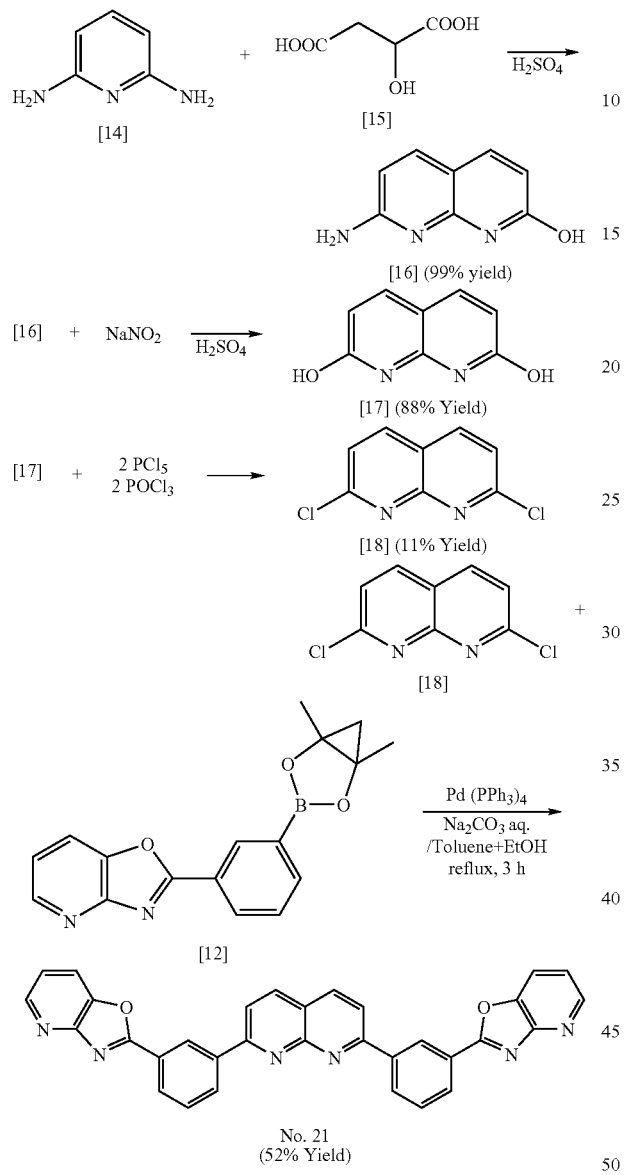

2,7-dichloro-1,8-naphthyridine [18] (white crystal) was obtained from [14] in a total yield of 9.6% by the synthesis method described in J. Org. Chem., 46, 833 (1981).

The following compounds were placed in a 100-ml three-necked flask, and the mixture was stirred under nitrogen atmosphere at room temperature. During the stirring, an aqueous solution of 1 g of sodium carbonate in 10 ml of water was added dropwise to the mixture.

1.57 g (4.88 mmol) of boronic acid pinacol ester [12]
0.49 g (2.46 mmol) of 2,7-dichloro-1,8-naphthyridine [18]
25 ml of toluene and 13 ml of ethanol Next, 0.28 g (0.24 mmol) of tetrakis(triphenylphosphine)palladium(0) was added to the mixture. After the mixture was stirred at room temperature for 10 minutes, the temperature of the mixture was increased to 78° C., and the mixture was stirred under heating and reflux for 3 hours. The reaction liquid was filtrated, and the resultant crude product was dissolved in 200 ml of chloroform at 70° C. The solution was purified with a silica gel column (chloroform/methanol=30/1), whereby 0.66 g of Exemplified Compound No. 21 (white crystal) was obtained (52% yield).

Synthesis Example 7

Synthesis of Exemplified Compound No. 32

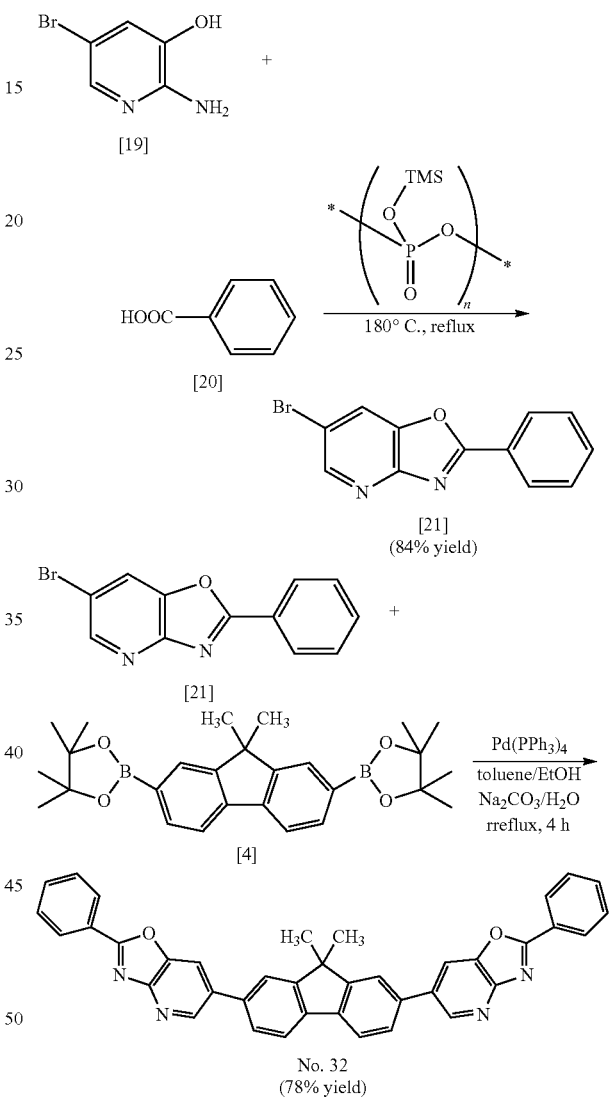

2-amino-5-bromopyridin-3-ol [19] was synthesized by the method described in Heterocycles, 55, 1329 (2001). Then, 6-bromo-2-phenyl-oxazolo[4,5-b]pyridine [21] (pale yellow crystal) was obtained from [19] and benzoic acid [20] in 84% yield.

The following compounds were placed in a 300-ml three-necked flask, and the mixture was stirred under nitrogen atmosphere at room temperature. During the stirring, an aqueous solution of 3 g of sodium carbonate in 30 ml of water was added dropwise to the mixture.

1.95 g (7.09 mmol) of 2-amino-5-bromopyridine-3-ol [19]
1.50 g (3.36 mmol) of a 9,9-dimethylfluorene-2,7-diboronic acid pinacol ester [4]
75 ml of toluene and 38 ml of ethanol Next, 0.39 g (0.34 mmol) of tetrakis(triphenylphosphine) palladium(0) was added to the mixture. After the mixture was stirred at room temperature for 10 minutes, the temperature of the mixture was increased to 78° C., and the mixture was stirred under heating and reflux for 4 hours. The reaction liquid was filtrated, and the resultant crude product was dissolved in 300 ml of chloroform at 70° C. The solution was purified with a silica gel column (toluene/acetic ether 5/1), whereby 1.53 g of Exemplified Compound No. 32 (white crystal) was obtained (78% yield).

Synthesis Example 8

Synthesis of Exemplified Compound No. 44

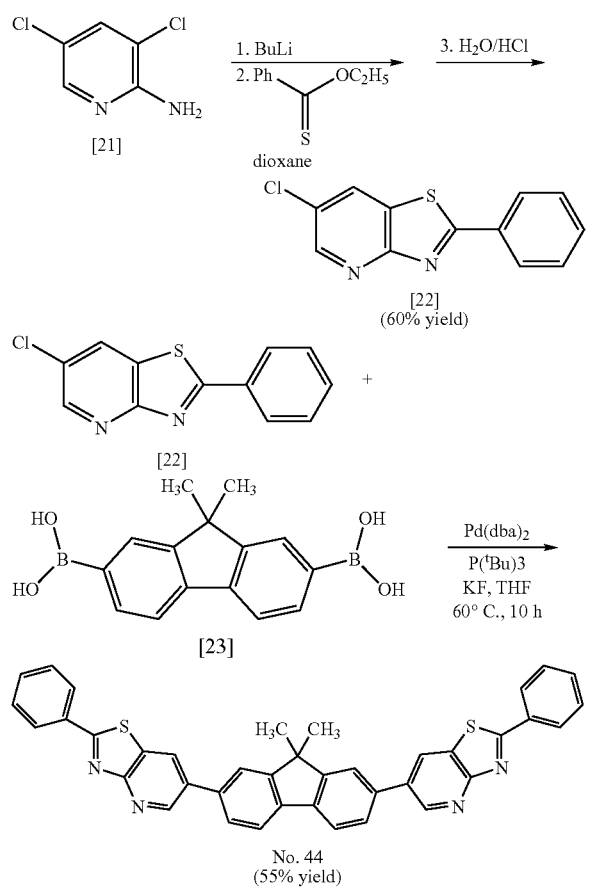

6-chloro-2-phenyl-thiazolo[4,5-b]pyridine [22] (pale yellow crystal) was obtained from 2-amino-3,5-dichloropyridine [21] in 60% yield by the synthesis method described in the following document:

Journal of Heterocyclic Chemistry, 24, 1765 (1987)

The following compounds were placed in a 300-ml three-necked flask, and the mixture was stirred under nitrogen atmosphere at room temperature. During the stirring, 0.31 g (0.53 mmol) of bis(dibenzylideneacetone)palladium(0) was added to the mixture.

2.88 g (11.70 mmol) of 6-chloro-2-phenyl-thiazolo[4,5-b]pyridine [22]

1.50 g (5.32 mmol) of 9,9-dimethylfluorene-2,7-diboronic acid [23]

1.85 g (31.9 mmol) of potassium fluoride 150 ml of THF

Next, 0.21 g (1.06 mmol) of tri-tertiary-butylphosphine was added dropwise to the mixture. After the mixture was stirred at room temperature for 10 minutes, the temperature of the mixture was increased to 60° C., and the mixture was stirred under heating and reflux for 10 hours. The reaction liquid was filtrated, and the resultant crude product was dissolved in 300 ml of chloroform at 70° C. The solution was purified with a silica gel column (toluene/acetic acid=6/1), whereby 1.79 g of Exemplified Compound No. 44 (white crystal) was obtained (55% yield).

Example 1

A device having the structure shown in FIG. 3 was produced.

A transparent conductive support substrate was prepared which had a film of indium tin oxide (ITO) with a thickness of 120 nm as the anode 2 formed on a glass substrate as the support 1 by a sputtering method. The transparent conductive support substrate was ultrasonically cleaned sequentially with acetone and isopropyl alcohol (IPA), subsequently washed with boiled IPA, was then dried, was further cleaned with UV/ozone, and was used.

Then, on the transparent conductive support substrate, a chloroform solution of a compound represented by the following structural formula was coated to form a film in a thickness of 11 nm by spin coating method to thereby form the hole-transporting layer 5.

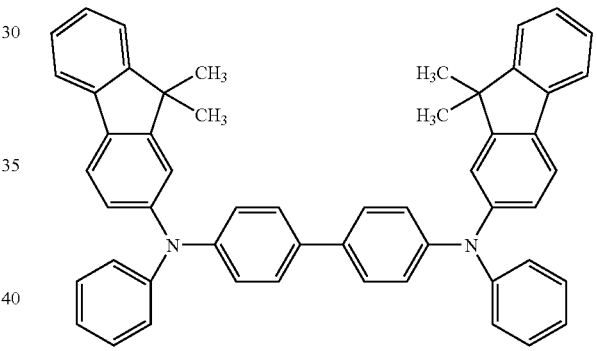

Further, an Ir complex and CBP (weight ratio of 10:900) represented by the following structural formulae were used and formed into a film having a thickness of 20 nm by means of a vacuum vapor deposition method, whereby the light-emitting layer 3 was formed. The film formation was performed under the conditions of a vacuum degree during deposition of $1.0 \times 10^{-4}$ Pa and a film forming rate of 0.1 to 0.2 nm/sec.

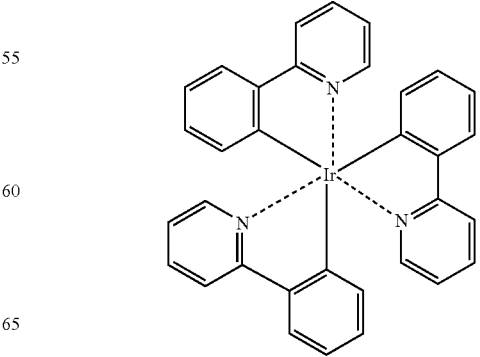

-continued

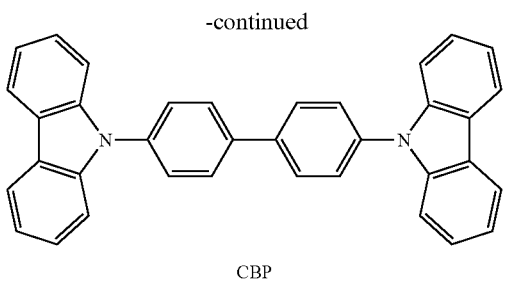

CBP

Further, Exemplified Compound No. 4 was used to form a film having a thickness of 20 nm by means of a vacuum vapor deposition method, whereby the electron-transporting layer 6 was formed. Film formation was performed under the conditions including a vacuum degree during deposition of $1.0 \times 10^{-4}$ Pa and a film forming rate of 0.1 to 0.2 nm/sec.

Next, lithium fluoride (LiF) was used to form a film having a thickness of 0.5 nm on the above organic layer by a vacuum vapor deposition method. Further, an aluminum film having a thickness of 120 nm was provided on the film by a vacuum vapor deposition method, whereby an organic light-emitting device having an Al—Li electrode (cathode 4) was produced. The vacuum degree during the deposition was $1.0 \times 10^{-4}$ Pa and the film forming rate was 0.05 nm/sec for lithium fluoride and 1.0 to 1.2 nm/sec for aluminum.

Further, the resultant was covered with a protective glass plate and encapsulated with an acrylic resin adhesive in a nitrogen atmosphere.

When a DC voltage of 7 V was applied to the thus obtained device with the ITO electrode (anode 2) being used as a positive electrode and the Al—Li electrode (cathode 4) being used as a negative electrode, a current flowed in the device at a current density of 40 mA/cm$^2$, and emission of green light was observed at a luminance of 5,900 cd/m$^2$.

Furthermore, when a voltage was applied to the device for 100 hours so that the current density was kept at 10.0 mA/cm$^2$, the device emitted light at a luminance of 1,500 cd/m$^2$ in an early stage and 1,100 cd/m$^2$ after the elapse of the 100 hours, which meant that the luminance degradation was small.

Examples 2 to 10

In each example, a device was produced by following the same procedure as in Example 1 with the exception that the compound shown in Table 1 was used instead of Exemplified Compound No. 4, and the produced device was similarly evaluated. Table 1 shows the results.

Comparative Examples 1 to 3

In each comparative example, a device was produced by following the same procedure as in Example 1 with the exception that the compound represented by the following structural formulae was used instead of Exemplified Compound No. 4, and the produced device was similarly evaluated. Table 1 shows the results.

Comparative Compound No. 1

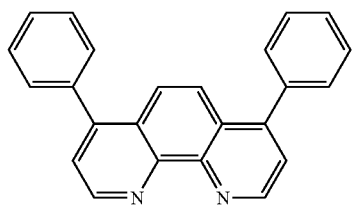

Comparative Compound No. 2

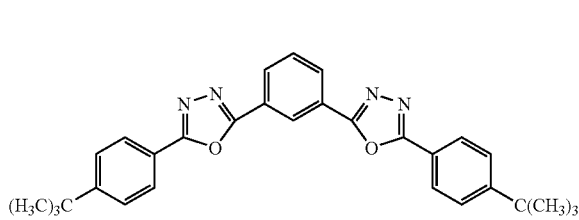

Comparative Compound No. 3

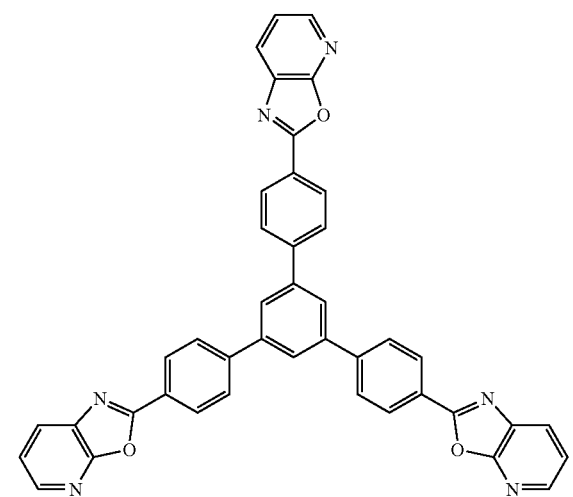

TABLE 1

| | | | | Evaluation for durability (Current density 10.0 mA/c m$^2$) | |
|---|---|---|---|---|---|
| | | Initial | | | Luminance |
| | Exemplified compound No. | Applied voltage (V) | Luminance (cd/m$^2$) | Initial luminance (cd/m$^2$) | after 100 hours (cd/m$^2$) |
| Ex. 1 | 4 | 7 | 5900 | 1500 | 1100 |
| Ex. 2 | 5 | 7 | 5600 | 1300 | 1080 |
| Ex. 3 | 9 | 7 | 4500 | 1050 | 800 |
| Ex. 4 | 10 | 7 | 4300 | 1080 | 850 |
| Ex. 5 | 37 | 7 | 4900 | 1300 | 1050 |
| Ex. 6 | 38 | 7 | 4700 | 1250 | 950 |
| Ex. 7 | 39 | 7 | 5200 | 1350 | 980 |
| Ex. 8 | 43 | 7 | 4600 | 1200 | 930 |
| Ex. 9 | 45 | 7 | 4800 | 1370 | 1020 |

TABLE 1-continued

| | | Evaluation for durability (Current density 10.0 mA/cm²) | | |
|---|---|---|---|---|
| | | | Initial | Luminance |
| | Exemplified compound No. | Applied voltage (V) | Luminance (cd/m²) | Initial luminance (cd/m²) | after 100 hours (cd/m²) |
| Ex. 10 | 47 | 7 | 5000 | 1420 | 1170 |
| Comp. Ex. 1 | Comp. Compd. No. 1 | 7 | 2200 | 1200 | 650 |
| Comp. Ex. 2 | Comp. Compd. No. 2 | 7 | 1600 | 1020 | 570 |
| Comp. Ex. 3 | Comp. Compd. No. 3 | 7 | 2600 | 1120 | 670 |

Example 11

A device having the structure shown in FIG. 3 was produced.

By following the same procedure as in Example 1, the hole-transporting layer 5 was formed on the transparent conductive support substrate.

Further, a fluorene compound represented by the following structural formula was formed into a film having a thickness of 20 nm by means of a vacuum vapor deposition method, whereby the light-emitting layer 3 was formed. The film formation was performed under the conditions of a vacuum degree during deposition of $1.0 \times 10^{-4}$ Pa and a film forming rate of 0.1 to 0.2 nm/sec.

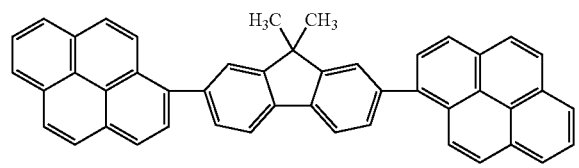

Further, Exemplified Compound No. 1 was formed into a film having a thickness of 20 nm by means of a vacuum vapor deposition method, whereby the electron-transporting layer 6 was formed. The film formation was performed under the conditions of a vacuum degree during deposition of $1.0 \times 10^{-4}$ Pa and a film forming rate of 0.1 to 0.2 nm/sec.

Next, the cathode 4 was formed in the same manner as in Example 1, followed by encapsulation.

When a DC voltage of 5 V was applied to the thus obtained device with the ITO electrode (anode 2) being used as a positive electrode and the Al—Li electrode (cathode 4) being used as a negative electrode, a current flowed in the device at a current density of 80 mA/cm², and emission of blue light was observed at a luminance of 4,200 cd/m².

Furthermore, when a voltage was applied to the device for 100 hours so that the current density was kept at 30 mA/cm², the device emitted light at a luminance of 1,590 cd/m² in an early stage and 1,100 cd/m² after the elapse of the 100 hours, which meant that the luminance degradation was small.

Examples 12 to 24

In each example, a device was produced by following the same procedure as in Example 11 with the exception that the compound shown in Table 2 was used instead of Exemplified Compound No. 1, and the produced device was similarly evaluated. Table 2 shows the results.

Comparative Examples 4 to 6

In each comparative example, a device was produced by following the same procedure as in Example 11 with the exception that Comparative Compound No. 1, 2, or 3 was used instead of Exemplified Compound No. 1, and the produced device was similarly evaluated. Table 2 shows the results.

TABLE 2

| | | Evaluation for durability (Current density 30 mA/cm²) | | |
|---|---|---|---|---|
| | | | Initial | Luminance |
| | Exemplified Compound No. | Applied voltage (V) | Luminance (cd/m²) | Initial luminance (cd/m²) | after 100 hours (cd/m²) |
| Ex. 11 | 1 | 5 | 4200 | 1590 | 1150 |
| Ex. 12 | 2 | 5 | 4080 | 1500 | 1100 |
| Ex. 13 | 3 | 5 | 4120 | 1550 | 1170 |
| Ex. 14 | 6 | 5 | 1130 | 960 | 800 |
| Ex. 15 | 7 | 5 | 1200 | 980 | 820 |
| Ex. 16 | 8 | 5 | 1220 | 1000 | 800 |
| Ex. 17 | 12 | 5 | 3400 | 1300 | 950 |
| Ex. 18 | 13 | 5 | 3200 | 1270 | 920 |
| Ex. 19 | 25 | 5 | 4120 | 1300 | 950 |
| Ex. 20 | 30 | 5 | 4080 | 1350 | 1050 |
| Ex. 21 | 32 | 5 | 2400 | 850 | 700 |
| Ex. 22 | 41 | 5 | 3800 | 1200 | 950 |
| Ex. 24 | 44 | 5 | 2200 | 870 | 700 |
| Comp. Ex. 4 | Comp. Compd. No. 1 | 5 | 1700 | 750 | 400 |
| Comp. Ex. 5 | Comp. Compd. No. 2 | 5 | 1100 | 550 | 200 |
| Comp. Ex. 6 | Comp. Compd. No. 3 | 5 | 900 | 500 | 200 |

Example 25

A device having the structure shown in FIG. 5 was produced.

The hole-transporting layer 5 was formed on the transparent conductive support substrate by following the same procedure as in Example 1. Subsequently, the light-emitting layer 3 was formed in the same manner as in Example 11.

Exemplified Compound No. 22 was formed into a film having a thickness of 20 nm by means of a vacuum vapor deposition method, whereby the hole-blocking layer 8 was formed. The film formation was performed under the conditions a vacuum degree during deposition of $1.0 \times 10^{-4}$ Pa and a film forming rate of 0.1 to 0.2 nm/sec.

Further, 2,9-bis(9,9-dimethyl-9H-fluoren-2-yl)-1,10-phenanthroline was formed into a film having a thickness of 20 nm by a vacuum vapor deposition method, whereby the electron-transporting layer 6 was formed. The degree of vacuum at the time of deposition was $1.0 \times 10^{-4}$ Pa and the film forming rate was 0.1 to 0.2 nm/sec.

Next, the cathode 4 was formed in the same manner as in Example 1, followed by encapsulation.

When a DC voltage of 5 V was applied to the thus obtained device with the ITO electrode (anode 2) being used as a positive electrode and the Al—Li electrode (cathode 4) being used as a negative electrode, a current flowed in the device at a current density of 82 mA/cm$^2$, and emission of blue light was observed at a luminance of 3,500 cd/m$^2$.

Furthermore, when a voltage was applied to the device for 100 hours so that the current density was kept at 30 mA/cm$^2$, the device emitted light at a luminance of 1,330 cd/m$^2$ in an early stage and 950 cd/m$^2$ after the elapse of the 100 hours, which meant that the luminance degradation was small.

Examples 26 to 33

In each example, a device was produced by following the same procedure as in Example 25 with the exception that the compound shown in Table 3 was used instead of Exemplified Compound No. 22, and the produced device was similarly evaluated. Table 3 shows the results.

Comparative Examples 7 to 9

In each comparative example, a device was produced by following the same procedure as in Example 25 with the exception that Comparative Compound No. 1, 2, or 3 was used instead of Exemplified Compound No. 22, and the produced device was similarly evaluated. Table 3 shows the results.

TABLE 3

| | Exemplified Compound No. | Applied voltage (V) | Initial Luminance (cd/m$^2$) | Evaluation for durability (Current density 30.0 mA/cm$^2$) Initial luminance (V) | Luminance after 100 hours (cd/m$^2$) |
|---|---|---|---|---|---|
| Ex. 25 | 22 | 5 | 3500 | 1330 | 950 |
| Ex. 26 | 26 | 5 | 3000 | 1300 | 870 |
| Ex. 27 | 27 | 5 | 3200 | 1350 | 1050 |
| Ex. 28 | 28 | 5 | 2900 | 1200 | 1010 |
| Ex. 29 | 29 | 5 | 2700 | 1250 | 950 |
| Ex. 30 | 36 | 5 | 2500 | 1050 | 820 |
| Ex. 31 | 37 | 5 | 2200 | 1010 | 800 |
| Ex. 32 | 38 | 5 | 2050 | 950 | 780 |
| Ex. 33 | 39 | 5 | 2200 | 980 | 770 |
| Comp. Ex. 7 | Comp. Compd. No. 1 | 5 | 900 | 650 | 300 |
| Comp. Ex. 8 | Comp. Compd. No. 2 | 5 | 700 | 450 | 200 |
| Comp. Ex. 9 | Comp. Compd. No. 3 | 5 | 850 | 400 | 200 |

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2006-312824, filed Nov. 20, 2006, which is hereby incorporated by reference herein in its entirety.

What is claimed is:

1. A heterocyclic compound of general formula [II]:

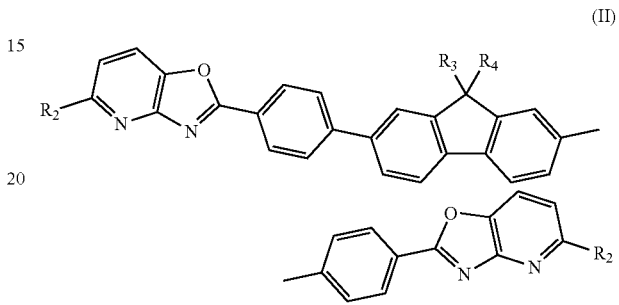

wherein R$_2$ is hydrogen or methyl and R$_3$ and R$_4$ are each independently hydrogen or methyl.

2. The heterocyclic compound according to claim 1, which is represented by the structural formula:

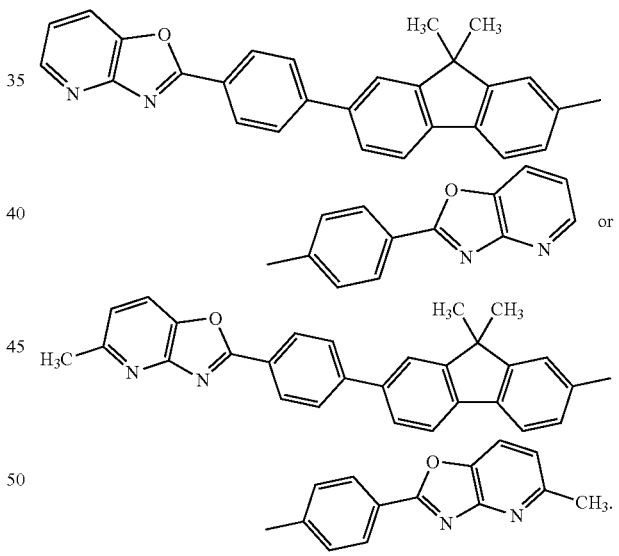

3. An organic light-emitting device comprising: a pair of electrodes including an anode and a cathode and a light-emitting layer and an organic compound layer interposed between the pair of electrodes, wherein the organic compound layer comprises the heterocyclic compound according to claim 1 and the organic compound is disposed between light emitting layer and the cathode.

* * * * *